(12) United States Patent
Bridges et al.

(10) Patent No.: US 9,689,828 B2
(45) Date of Patent: Jun. 27, 2017

(54) PASSIVE WIRELESS SENSOR

(71) Applicant: UNIVERSITY OF MANITOBA, Winnipeg (CA)

(72) Inventors: Greg E. Bridges, Winnipeg (CA); Douglas L. Thomson, Winnipeg (CA); Sharmistha Bhadra, Winnipeg (CA); Michael Freund, Winnipeg (CA)

(73) Assignee: UNIVERSITY OF MANITOBA (CA)

( * ) Notice: Subject to any disclaimer, the term of this patent is extended or adjusted under 35 U.S.C. 154(b) by 348 days.

(21) Appl. No.: 14/353,191

(22) PCT Filed: Oct. 10, 2012

(86) PCT No.: PCT/IB2012/055477
§ 371 (c)(1),
(2) Date: Apr. 21, 2014

(87) PCT Pub. No.: WO2013/057630
PCT Pub. Date: Apr. 25, 2013

(65) Prior Publication Data
US 2015/0053575 A1    Feb. 26, 2015

Related U.S. Application Data

(60) Provisional application No. 61/550,186, filed on Oct. 21, 2011.

(51) Int. Cl.
*G01N 15/06* (2006.01)
*G01N 33/00* (2006.01)
(Continued)

(52) U.S. Cl.
CPC ........... *G01N 27/302* (2013.01); *G01D 3/032* (2013.01); *G01K 7/24* (2013.01); *G01N 33/18* (2013.01);
(Continued)

(58) Field of Classification Search
CPC ........ G01N 15/06; G01N 33/00; G01N 33/48; G01N 27/00
(Continued)

(56) References Cited

U.S. PATENT DOCUMENTS 3,726,777 A    4/1973 Macur
4,861,453 A    8/1989 Matsuoka et al.
(Continued)

FOREIGN PATENT DOCUMENTS

CA    2799236    6/2011
CA    2799236 A1    6/2011
(Continued)

OTHER PUBLICATIONS

International Search Report and Written Opinion for PCT/IB2012/055477, issued by the Canadian Intellectual Property Office as the International Searching Authority, mailed Feb. 19, 2013; 10 pgs.
(Continued)

*Primary Examiner* — Brian J Sines
(74) *Attorney, Agent, or Firm* — Mueting, Raasch & Gebhardt, P.A.

(57) ABSTRACT

Systems, devices, and/or methods for use in passive wireless transmission of one or more parameters such as, e.g., pH, temperature, etc. are described. The systems, devices, and/or methods may use a passive sensor located proximate a material and an interrogator that may be used to interrogate the passive sensor and to receive a signal from the passive sensor representative of the one or more parameters.

15 Claims, 29 Drawing Sheets

(51) Int. Cl.

| | |
|---|---|
| G01N 33/48 | (2006.01) |
| G01N 27/00 | (2006.01) |
| G01N 27/30 | (2006.01) |
| H04Q 9/00 | (2006.01) |
| G01N 33/18 | (2006.01) |
| G01D 3/032 | (2006.01) |
| G01K 7/24 | (2006.01) |

(52) U.S. Cl.
CPC ........... *H04Q 9/00* (2013.01); *H04Q 2209/40* (2013.01); *H04Q 2209/47* (2013.01); *H04Q 2209/75* (2013.01)

(58) Field of Classification Search
USPC ................... 422/68.1, 82.01, 82.02; 436/43
See application file for complete search history.

(56) References Cited

U.S. PATENT DOCUMENTS

| | | | |
|---|---|---|---|
| 4,927,503 | A | 5/1990 | Polly |
| 5,015,355 | A | 5/1991 | Schiessl |
| 5,259,944 | A | 11/1993 | Feliu et al. |
| 5,403,550 | A | 4/1995 | Wietek |
| 5,792,337 | A | 8/1998 | Padovani et al. |
| 5,942,991 | A | 8/1999 | Gaudreau et al. |
| 5,964,992 | A | 10/1999 | Swette et al. |
| 6,387,424 | B2* | 5/2002 | Funk .............................. 426/113 |
| 6,806,808 | B1 | 10/2004 | Watters et al. |
| 7,034,660 | B2 | 4/2006 | Watters et al. |
| 7,124,039 | B2 | 10/2006 | Gadini et al. |
| 7,148,706 | B2 | 12/2006 | Srinivasan et al. |
| 7,248,182 | B2 | 7/2007 | Dudda et al. |
| 7,714,564 | B2 | 5/2010 | Wright et al. |
| 7,801,626 | B2 | 9/2010 | Moser |
| 2005/0107013 | A1* | 5/2005 | Gadini et al. .................... 451/42 |
| 2005/0109792 | A1* | 5/2005 | Fiorini et al. ..................... 222/1 |
| 2006/0037399 | A1 | 2/2006 | Brown |
| 2006/0125493 | A1 | 6/2006 | Subramanian et al. |
| 2007/0120572 | A1 | 5/2007 | Chen |
| 2008/0204275 | A1 | 8/2008 | Wavering et al. |
| 2009/0039864 | A1 | 2/2009 | Gordon |
| 2009/0058427 | A1 | 3/2009 | Materer et al. |
| 2009/0128169 | A1 | 5/2009 | Fay et al. |
| 2010/0198039 | A1 | 8/2010 | Towe |
| 2013/0106447 | A1* | 5/2013 | Bridges et al. ............... 324/700 |
| 2015/0053575 | A1 | 2/2015 | Bridges |

FOREIGN PATENT DOCUMENTS

| | | |
|---|---|---|
| WO | WO 2004/010104 A2 | 1/2004 |
| WO | WO 2011/153628 A1 | 12/2011 |

OTHER PUBLICATIONS

International Preliminary Report on Patentability for PCT/IB2012/055477, issued by the International Bureau of WIPO, mailed May 1, 2014; 8 pgs.
Andringa et al., "Unpowered wireless analog resistance sensor," *Proc SPIE Smart Structures and Materials*, 2004;5391:356-367.
Ativanichayaphong et al., "Development of an Implanted RFID Impedance Sensor for Detecting Gastroesophageal Reflux," in *Proc. IEEE International Conference on RFID*, Gaylord Texan Resort, Grapevine, TX, USA, Mar. 26-28, 2007, pp. 127-133.
Ativanichayaphong et al., "An implantable batteryless wireless impedance sensor for Gastroesophageal reflux diagnosis," in *Proc. of IEEE MTT-S International Microwave Symposium Digest*, 2010, pp. 608-611.
Barron et al., "The effects of temperature on pH measurement," Technical Services Department Reagecon Diagnostics Ltd, Shannon Free Zone, County Lake, Ireland, Rep. TSP-01 Issue 1, 2005.
Bhadra et al., "Electrode potential based coupled coil sensor for remote pH monitoring," *IEEE Sensors J.*, Nov. 2011;11(11):2813-2819.
Bhadra, Sharmistha "A Wireless Passive Sensor for In Vivo pH Monitoring," CMC Microsystems, TEXPO 2012; 1 Slide.
Bhadra et al., "A Wireless Passive Sensor for In Vivo pH Monitoring," CMC Microsystems, TEXPO 2012, Abstract; 2 pgs.
Bhadra et al., "Wireless Passive Sensor for pH Monitoring inside a Small Bioreactor," *IEEE Conference*, Minneapolis, MN, May 6-9, 2013; 4 pgs.
Bhadra et al., "Fluid Embeddable Coupled Coil Sensor for Wireless pH Monitoring in a Bioreactor," *IEEE Trans Instr Measur*, May 2014;63(5):1337-1346.
Bhadra et al., "A Wireless Passive Sensor for Treatment Compensated Remote pH Monitoring," *IEEE Sensors Journal*, Jun. 2013;13(6): 2428-2436.
Bhadra et al., "A Wireless Passive pH Sensor Based on pH Electrode Potential Measurement," *IEEE Conference*, Kona, HI, Nov. 1-4, 2010; 927-930; 4 pgs.
Bhadra et al., "A Wireless Passive Sensor for pH Monitoring Employing Temperature Compensation," *IEEE Conference*, Limerick, Oct. 28-31, 2011; 4 pgs; 1522-1525.
Bhadra et al., "A Wireless Passive pH Sensor for Real-Time In Vivo Milk Quality Monitoring," *IEEE Conference*, Taipei, Oct. 28-31, 2012; 4 pgs.
Bhadra et al., "Wireless Passive Sensor for Remote pH Monitoring," *J Nanotech Eng Med*, Feb. 1, 2011;2:011011-1-011011-4.
Bhadra, Sharmistha, "Coupled Resonant Coil Sensors for Remote Passive Monitoring Applications," Thesis submitted to the Faculty of Graduate Studies of the University of Manitoba, 2010; 149 pgs.
Du et al., "In situ measurement of Cl$^-$ concentrations and pH at the reinforcing steel/concrete interface by combination sensors," *Anal. Chem.*, Mar. 2006;78(9):3179-3185.
Dybko et al., "Assesment of water quality based on multiparameter fiber optic probe," *Sensors and Actuators B: Chemical*, Aug. 1998; 51(1-3): 208-213.
Engels et al., "Medical application of silicon sensors," *J. Phys E: Sci. Instrum*, 1983;16(10):987-994.
Frisby et al., "Development of an autonomous, wireless pH and temperature sensing system for monitoring pig meat quality," *Meat Science*, 2005;70:329-336.
Gill et al., "Investigation of thick-film polyaniline-based conductimetric pH sensors for medical applications," *IEEE Sensors J.*, May 2009; 9(5):555-562.
Grant et al., "A sol-gel based fiber optic sensor for local blood pH measurements," *Sensors and Actuators B: Chemical*, Nov. 1997; 45(1): 35-42.
Harms et al., "Bioprocess monitoring," *Current Opinion in Biotechnology*, Apr. 2002; 13(2): 124-127.
Horton et al., "A varactor-based inductively coupled wireless pH sensor," *IEEE Sensors J.*, Apr. 2011; 11(4):1061-1066.
Huang et al., "A passive radio-frequency pH-sensing tag for wireless food-quality monitoring," *IEEE Sensors J.*, Mar. 2012;12(3):487-495.
Huang et al., "A flexible pH sensor based on the iridium oxide sensing film," *Sensors and Actuators*, 2011;169:1-11.
Jain et al., "A wireless micro-sensor for simultaneous measurement of pH, temperature, and pressure," *Smart Materials and Structures*, 2001;10(2):347.
Jeevarajan et al., "Continuous pH monitoring in a perfused bioreactor system using an optical pH sensor," *Biotechnology and Bioengineering*, May 2002;78(4): 467-472.
Kermis et al., "Dual excitation ratiometric fluorescent pH sensor for noninvasive bioprocess monitoring: development and application," *Biotechnology Progress*, Sep. 2002;18(5):1047-1053.
Komives et al., "Bioreactor state estimation and control," *Current Opinion in Biotechnology*, Oct. 2003; 14(5): 468-474.
Kumar et al., "Minibioreactors," *Biotechnology Letters*, Jan. 2004;26(1):1-10.
Kurzweil, "Metal oxides and ion-exchanging surfaces as pH sensors in liquids: state-of-the-art and outlook," *Sensors*, 2009; 9: 4955-4985.
Lemos et al., "Soil calcium and pH monitoring sensor system," *J. Agric. Food Chem.*, Jun. 2007;55(12): 4658-4663.

(56) References Cited

OTHER PUBLICATIONS

Lin, J. "Recent development and applications of optical and fiber-optic pH sensors," *Trends in Analytical Chemistry*, Sep. 2000;19(9):541-552.

Loh et al., "Inductively Coupled Nanocomposite Wireless Strain and pH Sensors," *Smart Structures and Systems*, 2008;4(5): 531-548.

Nicolaou et al., "Rapid and quantitative detection of the microbial spoilage in milk using Fourier transform infrared spectroscopy and chemometrics," *The Analyst*, Jul. 2008; 133(10): 1424-1431.

Nolan et al., "Fabrication and characterization of a solid state reference electrode for electroanalysis of natural waters with ultramicroelectrodes," *Anal. Chem.*, Mar. 1997; 69: 1244-1247.

Nopper et al., "Wireless readout of passive *LC* sensors," *IEEE Transaction on Instrumentation and Measurement*, Sep. 2010; 59(9): 2450-2457.

Ong et al., "Remote query resonant-circuit sensors for monitoring of bacteria growth: application to food quality control," *Sensors*, 2002; 2: 219-232.

Ong et al., "A wireless, passive embedded sensor for real time monitoring of water content in civil engineering materials," *IEEE Sensors J.*, Dec. 2008; 8(12): 2053-2058.

Panova et al., "In situ fluorescence imaging of localized corrosion with a pH sensitive imaging fiber," *Anal. Chem.*, Apr. 1997; 69(8):1635-1641.

Papeschi et al., "An iridium-iridium oxide electrode for in vivo monitoring of blood pH changes," *Journal of Medical Engineering & Technology*, Mar. 1981;5(2):86-88.

Potyrailo et al., "Battery-free Radio Frequency Identification (RFID) Sensors for Food Quality and Safety," *J Agri Food Chem*, 2012;60:8535-8543.

Robinson and Clegg, "Improved determination of Q-factor and resonant frequency by a quadratic curve fitting method," *IEEE Transaction on Electromagnetic Compatibility*, May 2005;47(2):399-402.

Rubinstein et al., Polumer films on electrodes 4. Nafion-coated electrodes and electrogenerated chemiluminescence of surface-attached tris(2,2'- bipyridine)ruthernium(2+), *J of Amer Chem Soc*, Oct. 1980:102(21):6641-6642.

Soller et al., "Fiber optic sensing of tissue pH to assess low blood flow states," in *Proc. IEEE Sensors*, 2002:266-269.

Tsai, et al., "Noninvasive optical sensor technology in shake flasks for mammalian cell cultures," *BioProcess International*, Jan. 2012; 10(1):50-56.

Vasala et al., "A new wireless system for decentralized measurement of physiological parameters from shake flask," *Microbial Cell Factories*, Feb. 2006; 5(8):1-6.

Vuppu et al., "Economical wireless optical ratiometric pH sensor," *Meas. Sci. Technol.*, Feb. 2009; 20:045202(7pp).

Wilson and Walker, *Principles and Techniques of Biochemistry and Molecular Biology*, 7th ed., New York, Cambridge University Press, 2010, Cover page, title page and table of contents.

Wolthuis et al., "Development of medical fiber-optic pH sensor based on optical absorption," *IEEE Trans. Biomed. Eng.*, May 1992;39:531-537.

Yao et al., "A pH electrode based on melt-oxidized iridium oxide," *Journal of the electrochemical society*, 2001;148(4): H29-H36.

Zeng et al., "Time domain characterization of oscillating sensors: Application of frequency counting to resonance frequency determination," *Review of Scientific Instruments*, Dec. 2002;73(12): 4375-4380.

Apostolopoulos et al. "Consequences of steel corrosion on the ductility properties of reinforcement bar". 2008. *Construction and Building Materials*. 22(12):2316-2324.

Browne et al. 1983. Corrosion of Reinforcement in Concrete Construction. A.P. Crane, Ed., UK:Ellis Horwood Ltd. Title Page, Copyright Page, Table of Contents, pp. 193-222.

Butler et al. "Wireless passive, resonant-circuit, inductively coupled, inductive strain sensor". 2002. *Sensors and Actuators A*. 102(1):61-66.

Cabrera. "Deterioration of concrete due to reinforcement steel corrosion". 1996. *Cement and Concrete Composites*. 18(1):47-59.

Del Grosso et al. "Health monitoring for corrosion detection in reinforced concrete bridges". 2008. Bridge Maintenance, Safety, Management, Health Monitoring and Informatics—Koh & Frangopol (eds), Taylor and Francis Group, London. pp. 1532-1539.

"Embedded Corrosion Instrument" [Online]. <http://www.vatechnologies.com/eciNeed.htm>. Accessed Mar. 3, 2014. 2 pages.

Ervin et al. "Longitudinal guided waves for monitoring corrosion in reinforced mortar". 2008. *Measurement Science and Technology*. 19(5):055702. 19 pages.

Harpster et al. "A passive wireless integrated humidity sensor". 2002. *Sensors and Actuators A*. 95(2-3): 100-107.

Inaudi et al. "Reinforced Concrete Corrosion Wireless Monitoring System". 2009. 4th Intl. Conference on Structural Health Monitoring on Intelligent Infracture (SHMI-4). Zurich, Switzerland. pp. 1-10.

Miller et al. "Detection and imaging of surface corrosion on steel reinforcing bars using a phase-sensitive inductive sensor intended for use with concrete". 2003. *NDT & E International*. 36(1):19-26.

Nowak et al. "A novel architecture for remote interrogation of wireless battery free capactive sensors". 2006. *Presented at the 13th IEEE International Conference on Electronics, Circuits and Systems*. 4 pages.

Ong et al. "A wireless passive embedded sensor for real time monitoring of water content in civil engineering materials". 2008. *IEEE Sensors Journal*. 8(12):2053-2058.

Pasupathy et al. "Unpowered resonant wireless sensor nets for structural health monitoring" 2008. *Proc. IEEE Sensors*. pp. 697-700.

Reis et al. "Estimation of corrosion damage in steel reinforced mortar using waveguides". 2005. *ASME Journal of Pressure Vessel Technology*. 127:255-261.

Robinson et al. "Improved determination of Q-factor and resonant frequency by a quadratic curve fitting method". May 2005. IEEE Transaction on Electromagnetic Compatibility. 47(2):399-402.

Song et al. "Corrosion monitoring of reinforced concrete structures—a review" 2007. *International Journal of Electromechanical Science*. 2:1-28.

Tesche et al. "EMC analysis methods and computational models". 1997. New York: John Wiley & Sons, Inc. Title Page, Copyright Page, Table of Contents. 9 pages total.

Yeo et al. "Monitoring ingress of moisture in structural concrete using a novel optical-based sensor approach". 2006. *Journal of Physics: Conference Series*. 45:186-192.

Andringa et al. "Unpowered wireless corrosion sensor for steel reinforced concrete" 2005. *IEEE Sensors*. pp. 155-158.

"Embedded Corrosion Instrument" [Online]. http://www.vatechnologies.com/eciNeed.htm. Accessed Mar. 3, 2014. 2 pages.

Harpster et al. "A passive wireless integrated humidity sensor". 2002. *Sensors and Actuators A*. 95(2-3):100-107.

Ong et al. "Wireless passive resonant-circuit for monitoring food quality". 2002. *Proceedings of SPIE*. 4575:150-159.

Written Opinion, issued on Sep. 6, 2011 in related case PCT/CA2011/000679. 5 pages.

International Preliminary Report on Patentability, issued on Dec. 10, 2012, in related case PCT/CA2011/000679. 1 page.

International Search Report in related case PCT/CA2011/000679, issued on Sep. 6, 2011. 4 pages.

\* cited by examiner

PASSIVE WIRELESS SENSOR

CROSS-REFERENCE TO RELATED APPLICATION

This application is the §371 U.S. National Stage of International Application No. PCT/IB2012/055477, filed 10 Oct. 2012, which claims the benefit of U.S. Provisional Patent Application Ser. No. 61/550,186 filed 21 Oct. 2011, entitled "PASSIVE WIRELESS SENSOR INCLUDING TEMPERATURE COMPENSATION," each of which is incorporated herein by reference in its entirety.

BACKGROUND

The present disclosure relates generally to wireless sensing. More particularly, the present disclosure pertains to devices, systems, and methods for use in the passive wireless transmission of a sensed parameter (e.g., such as pH, etc.). Further, one or more exemplary devices, systems, and methods described herein include temperature compensation for the sensed parameter.

The outcome of a wide range of chemical and biological reactions are influenced by value, and thus, sensors capable of measuring pH may be desirable (see, e.g., J. B. E. Horton, S. Schweitzer, A. J. DeRouin and K. G. Ong, "A varactor-based inductively coupled wireless pH sensor," *IEEE Sensors J.*, vol. 11, no. 4, pp. 1061-1066, April 2011; and S. Bhadra, G. E. Bridges, D. J. Thomson and M. S. Freund, "Electrode potential based coupled coil sensor for remote pH monitoring," *IEEE Sensors J.*, vol. 11, no. 11, pp. 2813-2819, November 2011). It may be important to monitor and control pH in numerous fields such as structural health monitoring, environmental and food spoilage monitoring, industrial and chemical processing, and biomedical sensing (see, e.g., R.-G. Du, R.-G. Hu, R.-S. Huang and C.-J. Lin, "In situ measurement of Cl— concentrations and pH at the reinforcing steel/concrete interface by combination sensors," *Anal. Chem.*, vol. 78, no. 9, pp. 3179-3185. March 2006; J. M. L. Engels and M. H. Kuypers, "Medical application of silicon sensors," *J. Phys. E: Sci. Instrum.*, vol. 16, no. 10, pp. 987-994, 1983; J. Lin, "Recent development and applications of optical and fibre-optic pH sensors," *Trends in Analytical Chemistry*, vol. 19, no. 9, pp. 541-552, September 2000; and W. D. Huang, S. Deb, Y. S. Seo, S. Rao, M. Chiao and J. C. Chiao, "A passive radio-frequency pH-sensing tag for wireless food-quality monitoring," *IEEE Sensors J.*, available through IEEE early access). As maintaining proper pH in blood, the digestive tract, tissues, and fluids may be essential to support optimal health, numerous efforts have been dictated to develop pH sensors for biomedical sensing (see, e.g., S. A. Grant and R. S. Glass, "A Sol-gel based fiber optic sensor for local blood pH measurements," *Sensors and Actuators B: Chemical*, vol. 45, no. 1. pp. 35-42, November 1997; R. Wolthuis, D. McCrae, E. Saaski, J. Hartl and G. Mitchell, "Development of medical fiber-optic pH sensor based on optical absorption," *IEEE Trans. Biomed. Eng.*, vol. 39, pp. 531-537, May 1992; G. Papeschi, S. Bordi, M. Carlagrave, L. Criscione and F. Ledda, "An iridium-iridium oxide electrode for in vivo monitoring of blood pH changes," *Journal of Medical Engineering & Technology*, vol. 5, no. 2, pp. 86-88, March 1981; B. R. Soller, N. Cingo and T. Khan, "Fiber optic sensing of tissue pH to assess low blood flow states," in *Proc. IEEE Sensors*, 2002, pp. 266-269; T. Ativanichayaphong, J. Wang, W.-D. Huang, S. Rao, H. F. Tibbals, S.-J. Tang, S. J. Spechler, H. Stephanou and J.-C. Chiao, "Development of an implanted RFID impedance sensor for detecting Gastroesophageal reflux," in *Proc. IEEE International Conference on RFID*, 2007, pp. 127-133; T. Ativanichayaphong, S.-J. Tang, L.-C. Hsu, W.-D. Huang, Y.-S. Seo, H. F. Tibbals, S. Spechler and J.-C. Chiao, "An implantable batteryless wireless impedance sensor for Gastroesophageal reflux diagnosis," in *Proc. IEEE MIT-S International Microwave Symposium Digest*, 2010, pp. 608-611; E. I. Gill, A. Arshak, K. Arshak and O. Korostynska, "Investigation of thick-film polyaniline-based conductimetric pH sensors for medical applications," *IEEE Sensors J*, vol. 9, no. 5, pp. 555-562, May 2009). In environmental monitoring applications, pH sensors have been found useful for monitoring pH of the soil (e.g., pH of a soil solution) and drinking water (see, e.g., S. G. Lemos, A. R. Nogueira, A. Torre-Neto, A. Parra and J. Alonso, "Soil calcium and pH monitoring sensor system," *J. Agric. Food Chem.*, vol. 55, no. 12, pp. 4658-4663. June 2007; and A. Dybko, W. Wróblewski, E. Roźniecka, K. Poźniakb, J. Maciejewski, R. Romaniuk and Z. Brźozka, "Assessment of water quality based on multiparameter fiber optic probe," *Sensors and Actuators B: Chemical*, vol. 51 no. 1-3, pp. 208-213, August 1998). Further, pH sensors may be useful in many industrial manufacturing processes (see, e.g., J. Lin, "Recent development and applications of optical and fibre-optic pH sensors," *Trends in Analytical Chemistry*, vol. 19, no. 9, pp. 541-552, September 2000). pH sensors have further been applied to monitor pH change during food production (see, e.g., J. B. E. Horton, S. Schweitzer, A. J. DeRouin and K. G. Ong, "A varactor-based inductively coupled wireless pH sensor," *IEEE Sensors J.*, vol. 11, no. 4, pp. 1061-1066, April 2011), for food spoilage monitoring (see, e.g., W. D. Huang, S. Deb, Y. S. Seo, S. Rao, M. Chiao and J. C. Chiao, "A passive radio-frequency pH-sensing tag for wireless food-quality monitoring," *IEEE Sensors J.*, available through IEEE early access), and for localized corrosion (see, e.g., A. A. Panova, P. Pantano, D. R. Walt, "In situ fluorescence imaging of localized corrosion with a pH sensitive imaging fiber," *Anal. Chem.*, vol. 69, no. 8, pp. 1635-1641, April 1997). In structural health monitoring, the value of pH may be a crucial factor for assessing the deterioration of reinforced concrete structures. Further, in situ measurement of pH at the reinforcing steel/concrete interface has been used for monitoring the corrosion process (see, e.g., R.-G. Du, R.-G. Hu, R.-S. Huang and C.-J. Lin, "In situ measurement of Cl— concentrations and pH at the reinforcing steel/concrete interface by combination sensors," *Anal. Chem.*, vol. 78, no. 9, pp. 3179-3185. March 2006).

The sensors described herein may be used to measure parameters of a wide variety of materials such as milk or biomaterials. Milk is widely consumed across the world and its freshness is an important factor for public health. Milk spoilage may result in food poisoning and disease outbreaks, and as such, monitoring the quality of milk during transportation and storage may be beneficial (see, e.g., W. D. Huang, S. Deb, Y. S. Seo, S. Rao, M. Chiao and J. C. Chiao, "A passive radio-frequency pH-sensing tag for wireless food-quality monitoring," *IEEE Sensors J*, vol. 12, no. 3, pp. 487-495, March 2012).

Bacteria growth is a source of milk spoilage (see, e.g., W. D. Huang, S. Deb, Y. S. Seo, S. Rao, M. Chiao and J. C. Chiao, "A passive radio-frequency pH-sensing tag for wireless food-quality monitoring," *IEEE Sensors J.*, vol. 12, no. 3, pp. 487-495, March 2012; K. G. Ong, J. S. Bitler, C. A. Grimes, L. G. Puckett and L. G. Bachas, "Remote query resonant-circuit sensors for monitoring of bacteria growth: application to food quality control," *Sensors*, vol. 2, pp. 219-232, 2002; and N. Nicolaou and R. Goodacre, "Rapid and quantitative detection of the microbial spoilage in milk using Fourier transforminfrared spectroscopy and chemometrics," *The Analyst*, vol. 133, no. 10, pp. 1424-1431, July 2008). Standard plate count or psychrotrophic bacteria count may be used to monitor bacteria concentration in milk. However, standard plate count or psychrotrophic bacteria count methods may be time consuming and labor intensive. Further, although microbiological impedance devices may provide a less labor intensive way to estimate bacteria count, such microbiological impedance devices can also introduce contamination (see, K. G. Ong, J. S. Bitler, C. A. Grimes, L. G. Puckett and L. G. Bachas, "Remote query resonant-circuit sensors for monitoring of bacteria growth: application to food quality control," *Sensors*, vol. 2, pp. 219-232, 2002).

Another common milk freshness monitoring method may utilize a gas sensor. Gas sensors may be made of metal oxide semiconductors, conducting organic polymers or piezoelectric crystals, and may rely on changes of conductivity of sensing films induced by the adsorption of gases and subsequent surface reactions that are produced by milk during spoilage processes. Gas sensors may be easily affected by environmental conditions such as moisture and temperature (see, e.g., W. D. Huang, S. Deb, Y. S. Seo, S. Rao, M. Chiao and J. C. Chiao, "A passive radio-frequency pH-sensing tag for wireless food-quality monitoring," *IEEE Sensors J.*, vol. 12, no. 3, pp. 487-495, March 2012). As such, a simple, cost effective and remote milk quality monitoring sensor that can be embedded in the milk container as milk freshness indicator may be desired.

Bioreactors are most commonly used for carrying out bioprocesses to produce many commodities and chemicals. During bioprocesses, optimal cell growth may depend on pH control and many cells produce acids as a metabolic by-product. Therefore, monitoring and regulating the pH of the biological medium may be important for successful bioreactor operation (see, e.g., P. Harms, Y. Kostov and G. Rao, "Bioprocess monitoring," *Current Opinion in Biotechnology*, vol. 13, no. 2, pp. 124-127, April 2002; and A. S. Jeevarajan, S. Vani, T. D. Taylor and M. M. Anderson, "Continuous pH monitoring in a perfused bioreactor system using an optical pH sensor," *Biotechnology and Bioengineering*, vol. 78, no. 4, pp. 467-472, May 2002).

Sterilizable electrochemical pH probes may be used for bioprocess monitoring. Such electrochemical pH probes, however, may require a wired connection for data exchange, and, as such, are inherently invasive. Shake flasks and test tubes are regularly used in academia as well as in industry for selection and bioprocess development. The use of wired pH probes for multiple reactors (e.g., to simultaneously monitor several shake flasks) may require a proportional increase of wiring, cost and complexity, and as such, non-invasive sensors may be an attractive alternative (see, e.g., S. Vuppu, Y. Kostov and O. Rao, "Economical wireless optical ratiometric pH sensor," *Meas. Sci. Technol.*, vol. 20, pp. 045202(7pp), February 2009; C. Komives and R. S. Parker, "Bioreactor state estimation and control," *Current Opinion in Biotechnology*, vol. 14, no. 5, pp. 468-474, October 2003; A. Vasala, J. Panula, M. Bollóa, L. Illmann, C. Hálsig and P. Neubauer, "A new wireless system for decentralized measurement of physiological parameters from shake flask," *Microbial Cell Factories*, vol. 5, no. 8, pp. 1-6, February 2006; and S. Kumar, C. Wittniann and E. Heinzle, "Minibioreactors," *Biotechnology Letters*, vol. 26, no. 1, pp. 1-10, January 2004).

Very few non-invasive pH sensors may be used inside bioreactors because most pH sensors cannot endure the harsh bioprocess environment inside a bioreactor, e.g., because the medium may permeate through and damage the sensor. Further, the fluid medium culture may not be well defined, which may interfere with the sensor readings. Moreover, sterilization of the sensors used in bioprocesses may be required to avoid medium contamination so as to not interfere with metabolism (see, e.g., P. Harms, Y. Kostov and G. Rao, "Bioprocess monitoring," *Current opinion in Biotechnology*, vol. 13, no. 2, pp. 124-127, April 2002). Non-invasive optical sensors based on absorbance or fluorescence from pH-sensitive dyes have been used inside bioreactors. Optical sensors, however, may suffer from a narrow operating range and drifting over time (see, e.g., W.-L Tsai, S. L. Autsen, J. Ma, T. Hudson and J. Luo, "Noninvasive optical sensor technology in shake flasks for mammalian cell cultures," *BioProcess International*, vol. 10, no. 1, pp. 50-56, January 2012; and H. R. Kermis, Y. Kostov, P. Harms and G. Rao, "Dual excitation ratiometric fluorescent pH sensor for noninvasive bioprocess monitoring: development and application," Biotechnology Progress, vol. 18, no. 5, pp. 1047-1053, September 2002).

SUMMARY

The disclosure herein relates to passive sensors that can measure one or more parameters such as pH, temperature, etc. and wirelessly transmit such measured parameters. An interrogator may interrogate the passive sensors to energize the sensors, and then receive the one or more signals representative of the measured parameters. The interrogator may then use the one or more parameters to generate values based on the received signals. The interrogator may further adjust, or compensate, one of the parameters based on another parameter. For example, the interrogator may adjust, or compensate, a receive pH value based on a received temperature value since, e.g., pH readings may be temperature sensitive.

One exemplary embodiment includes an integrated wireless passive sensor for remote pH monitoring employing temperature compensation. The sensor may be a RLC resonant circuit that includes a planar spiral inductor connected in parallel to a temperature dependent resistor (e.g., thermistor) and a voltage dependent capacitor (e.g., varactor). The sensor may further include a pH combination electrode including an iridium/iridium oxide ($Ir/IrO_x$) sensing electrode and a silver/silver chloride (Ag/AgCl) reference electrode, e.g., that may be connected in parallel with the varactor. A potential difference change across the electrodes due to pH variation of the solution being measured (e.g., which the electrodes are exposed to) may change the voltage-dependent capacitance, and thus, may shift the resonant frequency.

Further, the temperature of the solution may affect the resistance of the sensor and may change the quality factor of the sensor. An interrogator coil may be inductively coupled to the sensor inductor and may remotely track the resonant frequency and quality factor of the sensor. In at least one embodiment, the sensor may measure pH from about a pH of 1.5 to a pH of about 12 with temperature over from about 25 degrees Celsius (° C.) to about 55° C. In at least one embodiment, by employing temperature compensation, the accuracy of a pH measurement may be demonstrated to be within plus or minus 0.1 pH. In at least one embodiment, the response time of the sensor may be limited by the response time of the pH combination electrode and may be less than about 1 second to be within plus or minus 0.1 pH accuracy. Further, the exemplary sensors described herein may overcome pH measurement error due to the temperature dependence of the electrode-based passive pH sensors, and as a result, the exemplary sensors described herein may have applications in remote pH monitoring where temperature varies aver a wide range.

Another exemplary embodiment is a wireless passive sensor for remote in-fluid milk pH measurement. The sensor may include a planar spiral inductor connected, or electrically coupled, in parallel to a varactor forming a LC resonant circuit. The sensor may further include a pH combination electrode including (e.g., made of) an iridium/iridium oxide sensing electrode and a silver/silver chloride reference electrode, which may be also connected, or electrically coupled, in parallel to the varactor. As the pH of the milk changes during spoilage, a voltage across the electrodes may vary, shifting the resonant frequency of the sensor. For in-fluid monitoring, the sensor may be sandwiched between dielectric spacers for encapsulation and to reduce parasitic capacitive coupling and eddy current loss. In at least one embodiment, the sensor may be hermetically-sealed (e.g., sealed to prevent fluid ingress to the sensor circuitry) in, e.g., a low-loss material. A low-loss material may allow the passive transmission of a signal representative of a parameter such as, e.g., pH, to be transmitted from and/or to inside of the low-loss material to/from outside of the low-loss material, which may be located adjacent, or next to, a wall of a container (e.g., touching, or having contact with, a wall of a container such that no fluid material is located between the low-loss material and the wall of the container). In other words, the low-loss material may not restrict the wireless transmission of a signal from and to sensor circuitry encapsulated, or contained within, the low-loss material. In at least one embodiment, the low-loss material surrounding the sensor may be located in the fluid and in proximity with, or to, the wall of the container but with fluid between the sensor and the wall.

Further, the resonant frequency of the sensor may be tracked remotely by an interrogator coil coupled to the sensor inductor. In at least one embodiment, measurement of milk pH may be monitored with at least about 100 kilohertz (kHz)/pH sensitivity and at least about 0.12 pH accuracy from a pH of 6.8 to a pH of 4.4.

One exemplary embodiment is a wireless passive pH sensor for continuous remote bioprocess monitoring. The sensor may be small enough to fit inside a small bioreactor or test tube and may include a planar spiral inductor connected in parallel to a varactor forming a LC resonant circuit. Similar to the in-fluid pH measurement sensor, the circuitry for the pH sensor for continuous remote bioprocess monitoring may be hermetically sealed and/or encapsulated, or contained within, a low-loss material. More specifically, the sensor may be hermetically sealed to encapsulate and reduce parasitic capacitive coupling and eddy current loss.

The sensor may further include a pH combination electrode comprising/including (e.g., made of) an iridium/iridium oxide sensing electrode and a silver/silver chloride reference electrode (e.g., a silver/silver chloride electrode with a nation coating), which are connected, or electrically coupled, in parallel to varactor. As the pH of the medium inside the bioreactor or test tube changes (e.g., during spoilage), the voltage across the electrodes varies, shifting the resonant frequency of the sensor. The resonant frequency of the sensor may be tracked remotely by an interrogator inductor inductively coupled to the sensor. In at least one embodiment, the sterilizable sensor may be configured to monitor pH of a medium with at least about a 2.46 megahertz (MHz)/pH sensitivity and a maximum deviation of at least about 0.07 pH from a commercial pH probe measurement from a pH of 6.5 to a pH of 5.26.

One exemplary system for use in wireless transmission of a parameter may include a passive sensor locatable proximate a material (e.g., perishable material) and an interrogator portion locatable proximate the passive sensor device. The passive sensor device may include a sensing portion and a circuit portion. The sensing portion may be configured to be used to measure a parameter of the material and at least a portion of the sensing portion may be exposable to the material. The circuit portion may be electrically coupled to the sensing portion and configured to measure the parameter using the sensing portion and to measure a temperature proximate the sensing portion. The circuit portion may be further configured to wirelessly transmit a signal (e.g., a single signal) representative of the measured parameter and the measured temperature when energized. The interrogator portion may include interrogating circuitry configured to wirelessly transmit energy to the circuit portion of the passive sensor device (e.g., wirelessly transmit energy to the circuit portion using at least one of a swept frequency source and a time-gated swept frequency source) and to wirelessly receive the signal representative of the measured parameter and the measured temperature from the circuit portion of the passive sensor device (e.g., wirelessly receive the signal representative of the measured parameter and the measured temperature after a selected period of time has elapsed following energization of the circuit portion of the passive sensor device by the wirelessly transmitted energy). Further, the interrogating circuitry may be further configured to generate a temperature-compensated value (e.g., pH) of the parameter based on the received signal (e.g., configured to determine the measured parameter and the measured temperature from at least one of the frequency response of the signal and the time response of the signal).

One exemplary passive sensor device for use in wireless transmission of a parameter of a material (e.g., perishable material) may include a sensing portion and a circuit portion. The sensing portion may be configured to be used to measure a parameter of a material and at least a portion of the sensing portion is exposable to the material. The circuit portion may be electrically coupled to the sensing portion and may be configured to measure the parameter using the sensing portion and to measure a temperature proximate the sensing portion. The circuit portion may be further configured to wirelessly transmit a signal (e.g., a single signal) representative of the measured parameter and the measured temperature when energized by an interrogator portion locatable proximate the circuit portion. The measured parameter and the measured temperature may correlate to a temperature-compensated value (e.g., pH) of the parameter.

One exemplary passive sensor device for use in fireless transmission of a parameter of a fluid material (e.g., perishable material) within a container defining at least one wall may include a sensing portion and a hermetically-sealed circuit portion. The sensing portion may be configured to be used to measure a parameter of a fluid material within a container, and at least a portion of the sensing portion is exposable to the fluid material. The hermetically-sealed circuit portion may be configured to be located at least partially within the container adjacent at least one wall of the container and electrically coupled to the sensing portion. The circuit portion may be further configured to measure the parameter of the fluid material within the container using the sensing portion, and to wirelessly transmit a signal representative of the measured parameter (e.g., pH) when energized by an interrogator portion locatable proximate the circuit portion.

One exemplary method of wireless transmission of a parameter may include providing a passive sensor device proximate a material (e.g., perishable material). The passive sensor device may include a sensing portion configured to be used to measure a parameter of the material and a circuit portion electrically coupled to the sensing portion. At least a portion of the sensing portion is exposed to the material. The circuit portion may be configured to measure the parameter using the sensing portion and to measure a temperature proximate the sensing portion. The exemplary method may further include locating an interrogator proximate the passive sensor device, wirelessly transmitting energy from the interrogator to the circuit portion of the passive sensor device (e.g., wirelessly transmit energy to the circuit portion using at least one of a swept frequency source and a time-gated swept frequency source), wirelessly transmitting a signal (e.g., a single signal) representative of the measured parameter and the measured temperature from the circuit portion of the passive sensor device, and generating a temperature-compensated value (e.g., pH) of the parameter based on the signal representative of the measured parameter and the measured temperature (e.g., configured to determine the measured parameter and the measured temperature from at least one of the frequency response of the signal and the time response of the signal).

In one or more exemplary systems, devices, or methods, the sensing portion may include a first electrode exposable to the material and a second electrode exposable to the material (e.g., at least one of the first electrode and the second electrode may include a nation layer). The circuit portion may be electrically coupled to the first electrode and the second electrode and may be further configured to measure a potential between the first electrode and the second electrode.

In one or more exemplary systems, devices, or methods, the circuit portion may be configured such that at least one of the quality factor at the resonant frequency of the signal shifts in response to changes in the measured temperature proximate the sensing portion and the resonant frequency of the signal shifts in response to changes in the measured parameter. Further, the circuit portion may be encapsulated by a low-loss material, encapsulated by polymer material, at least partially embedded within a container where the container at least partially contains the material, at least a portion of the passive sensor device is part of packaging for a perishable material, etc. Still further, the circuit portion of the passive sensor device may include at least one of an inductive loop coupled to a capacitor (e.g., a varactor diode) that changes capacitance based on the measured parameter, an inductive loop coupled to a capacitor (e.g., a varactor diode) that changes capacitance based a potential difference between two electrodes exposed to the material, and an inductive loop coupled to a thermistor that changes resistance based on the temperature proximate the sensing portion.

In one or more exemplary systems, devices, or methods, the material may be at least one of a fluid or solid used in a manufacturing process, biological material, concrete, a perishable material, and an effluent or waste product.

The above summary is not intended to describe each embodiment or every implementation of the present disclosure. A more complete understanding will become apparent and appreciated by referring to the following detailed description and claims taken in conjunction with the accompanying drawings.

DESCRIPTION OF THE EMBODIMENTS

Figure 1:
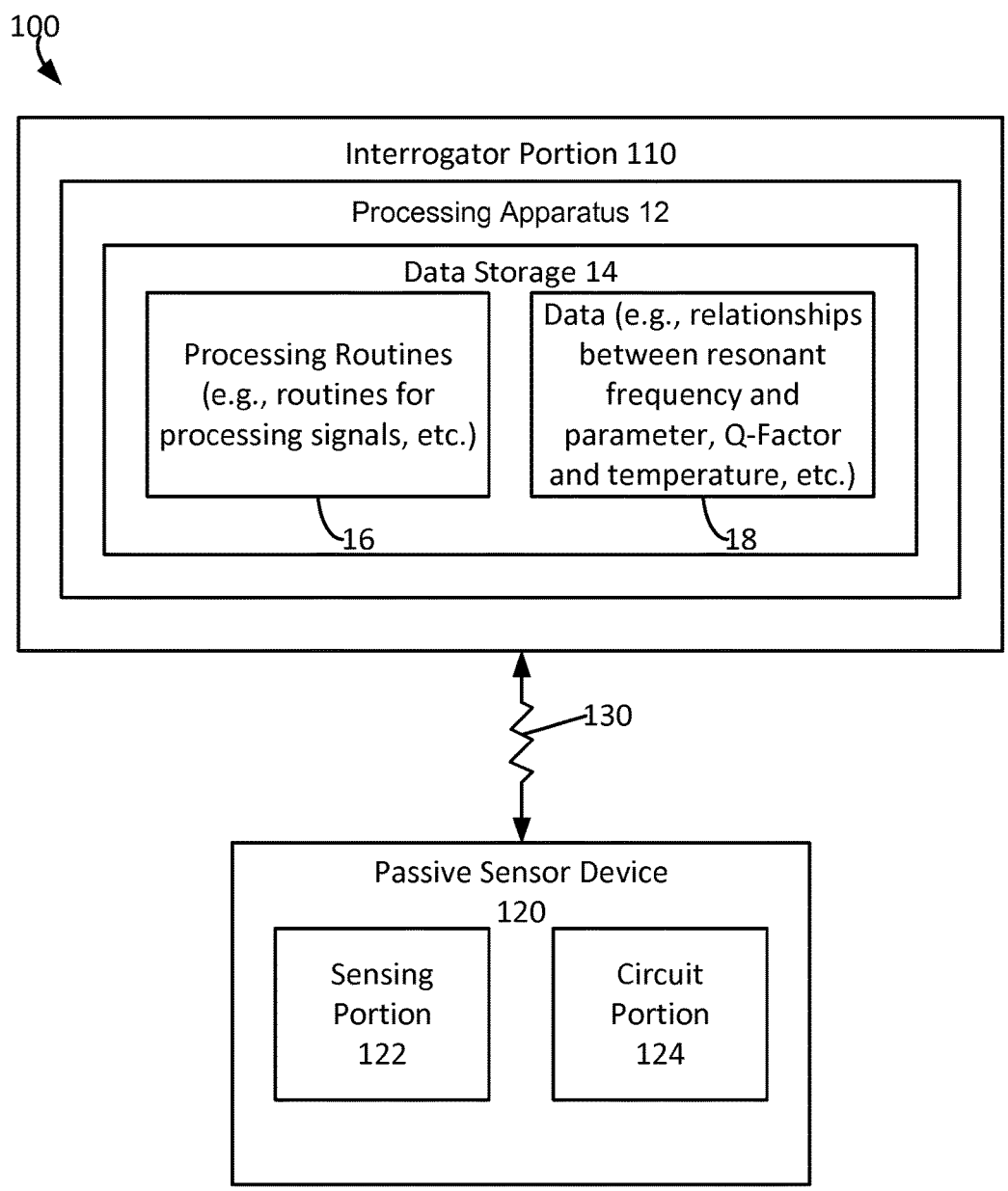
FIG. 1 is a block diagram depicting an exemplary system for use in wireless transmission of parameter.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural Changes may be made without departing from (e.g., still falling within) the scope of the disclosure presented hereby.

Exemplary methods, devices, and systems shall be described with reference to FIGS. 1-28. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

A pH sensor may utilize a pH combination electrode, which generally includes a sensing and a reference electrode. The sensing electrode may provide a potential that is dependent on pH of the sample while the reference electrode ideally provides a pH independent potential. The potential difference across the sensing and reference electrode $V_{pH}$, can be expressed by the Nernst equation as (see, e.g., P. Kurzweil, "Metal oxides and ion-exchanging surfaces as pH sensors in liquids: state-of-the-art and outlook," Sensors, vol. 9, pp. 4955-4985, 2009):

$$V_{pH} = V_0 - \frac{RT}{nF} pH. \tag{1}$$

In Equation (1), T is the sample temperature in Kelvin, R is the universal gas constant (8.314472 J K$^{-1}$ mol$^{-1}$), F is the Faraday constant (9.64853399×10$^4$ C mol$^{-1}$), p is the pH value of the solution, n is the number of moles of electrons transferred in the electrochemical cell reaction, and $V_0$ is the standard cell potential difference at temperature T. For a constant temperature, a pH combination electrode may provide a potential difference that is proportional to the value of the sample. Thus, it may be desired that temperature be accounted for in order to provide accurate measurements in electrode-based pH sensors.

Further, electrode-based pH sensors may include a wired electrical connection directly to a potentiometer or pH meter, which may not be suitable in situations where electrical connection to the measuring device is inconvenient or impossible, as in embedded or remote monitoring applications.

An exemplary system 100 for use in the wireless transmission of at least one parameter (e.g., pH, temperature, etc.) is depicted in FIG. 1. Generally, the system 100 includes an interrogator portion (block 110) and a passive sensor device (block 120). Although the interrogator portion (block 110) and the passive sensor device (block 120) are described herein as being a portion and a device, respectively, of system 100, it is to be understood the interrogator portion (block 110) may be described as being a "device" and the passive sensor device (block 120) may also be described herein as being a "portion," such as an interrogator device (block 110) and a sensor portion (block 120).

The passive sensor device (block 120) may be located embedded in, in contact with, adjacent to, or otherwise proximate a material such as, e.g., perishable material, concrete, material used in manufacturing or chemical processes, solid or fluid material used in production processes, animal or human tissue (e.g., biological tissue), biological fluids, fluids, effluent or waste material, solid or liquid food product, material with a biological reactor, material within a fermentation vessel, any other material locatable within any environment that may require environmental monitoring, etc., of which a parameter may be measured such as, e.g., pH, temperature, corrosion potential, ion concentration (e.g., chloride ion concentration, etc.), humidity, electric permittivity, electrical conductivity, pressure, strain, and/or any parameter that may produce a change in a capacitive sensor. Further, the passive sensor device (block 120) may be included, or at least partially embedded, with a container, or packaging, that holds the material, in at least one embodiment, the passive sensor device (block 120) may be completely embedded, or implanted, in the material to be measured. In at least one embodiment, at least a portion of the passive sensor device (block 120) is embedded in a polymer material (e.g., plastic wrap) or a paper material (e.g., cardboard) wrapping at least a portion of perishable material such as a food product (e.g., milk, meat, vegetables, etc.).

Fluid materials may affect electromagnetic waves, and thus, can cause problems with wireless sensors placed in proximity to or inside fluids. The large dielectric constant of polar fluids such as water can cause detuning of resonant coil type sensors and the loss imposed by the fluid can degrade a signal between a wireless interrogator and a sensor. The electrical properties of a non-magnetic material at a given frequency are specified by its complex permittivity, with the real part, Er', related to the polarization of the material in an applied electric field and the imaginary part, Er", related to the loss mechanisms in the material. The loss is often specified through a "loss tangent," Er"/Er' for non-conductive media, with large values indicating larger loss.

To reduce the effects of the fluid material on the passive sensor device (block 120), at least the circuit portion (block 124) of the passive sensor device (block 120) may be surrounded (e.g., contained, encapsulated, held, etc.) by a fixed dielectric constant, low-loss material, e.g., so that the electromagnetic field from the circuit portion (block 124) (e.g., such as a coil) does not penetrate into the fluid.

Low-loss materials that may be used with the passive sensor devices (block 120) described herein may include polystyrene, acrylonitrile butadiene styrene (ABS), plexiglass, air, silicon, any combination of the aforementioned materials, etc. In at least one embodiment, the low-loss material may have a loss tangent less than or equal to about 0.002. Further, since air is almost lossless, a container including, or made of, a low-loss material defining an air-filled cavity may be used to surround the circuit portion (block 124) (e.g., at least a portion such as the circuit portion (block 124) of the sensor device (block 120) may be located inside of the cavity). Still further, the low-loss material may define a wall thickness separating the circuit portion (block 124) from outside of the low-loss material. The wall thickness of the low-loss material may depend on the type of material being used. In at least one embodiment, the wall thickness may be less than or equal to about 6 millimeters (mm).

Further, sensor device (block 120) may be configured such that it is locatable adjacent a wall of a container containing the material being monitored such that, e.g., no material (i.e., the material being monitored) may be located between the coil of the circuit portion (block 124) and the wall. For example, the low-loss material surrounding the circuit portion (block 124) may be adjacent the wall of the container. Further, for example, the low-loss material surrounding the circuit portion (block 124) may be coupled (e.g., removably coupled to) the wall of the container. In at least one embodiment, the sensor device (block 120) may be weighted (e.g., have an increased mass) such that the sensor device (block 120) has a greater density than the material being monitored, e.g., so that the sensor device (block 120) does not float on top of the material being monitored. For example, the sensor device (block 120) may be configured to have a mass such that the sensor device (block 120) may locate itself on the bottom of a container, adjacent the bottom wall of the container, with, e.g., no material (i.e., material being monitored) located between at least the coil of the circuit portion (block 124) of the sensor device (block 120). Still further, the sensor device (block 120) may be configured such that it is fixed inside a container such that fluid is located between the sensor and the container wall.

Additionally, since the passive sensor device (block 120) may be used to measure one or more parameters of fluid materials, at least the circuit portion (block 124) may be hermetically sealed from moisture ingress of the fluid material using, e.g., the low-loss material surrounding the circuit portion (block 124). In at least one embodiment, the circuit portion (block 124) may be located inside of cavity defined by low-loss materials (e.g., one or more polymers, poly (methyl methacrylate), PLEXIGLAS, etc.) such that moisture or fluid may not contact the circuit portion (block 124).

The interrogator portion (block 110) may be used in conjunction with the passive sensor device (block 120). For example, the interrogator portion (block 110) may be located outside of the material but still proximate to the passive sensor device (block 120) such that it may interrogate the passive sensor device (block 120). The interrogator portion (block 110) may include interrogating circuitry (e.g., analog and/or digital hardware and/or software) configured to wirelessly transmit energy (e.g., through induction) and to wirelessly receive data signals.

The passive sensor device (block 120) may include a sensing portion (block and a circuit portion (block 124). The passive sensor device (block 120) may be defined as being "passive" because it does not include a power source. In at least one embodiment, each of the sensing portion (block 122) and the circuit portion (block 124) are passive, and therefore, do not include a power source. In other words, for the passive sensor device (block 120), and each of the sensing portion (block 122) and the circuit portion (block 124), to function, power may be provided from an external source such as energy delivered to the passive sensor device (block 120) through induction (e.g., the circuit portion (block 124) may include an inductive loop for receiving energy).

Generally, the sensing portion (block 122) may be configured to sense one or more parameters of a material. For example, the sensing portion (block 122) may include a capacitive sensor configured to sense one or more parameters of the material. The capacitive sensor may be configured to be sensitive to electric voltage and may include a first electrode and second electrode (e.g., each electrode may include one or more metals). Each of the first electrode and the second electrode may be exposed to the material and spaced apart from one another (e.g., not in contact with one another) such that a potential may be measured between the first electrode and the second electrode, e.g., through the material.

The type of electrodes may be chosen to produce a potential difference sensitive to pH, chloride, or other ion concentration. Although a voltage sensitive capacitive sensor is described herein, any type of sensor (e.g., capacitive sensor) may be used in the sensing portion (block 122) of the passive sensor device (block 120) to measure any type of parameter. In at least one embodiment, the sensing portion (block 122) may include a polymer-based capacitive sensor configured to change its capacitance in response to a specific chemical. In at least one embodiment, the sensing portion (block 122) is configured to measure the pH of a material (e.g., a capacitive pH sensor utilizing a first electrode and a second electrode).

The first electrode may be referred to as the sensing electrode and may include one or more materials such as, e.g., iridium, iridium oxide, metal, metal oxide, tungsten, tungsten oxide, antimony, antimony oxide, glass (e.g. common glass electrode), any combination of the aforementioned materials, etc. The second electrode may be referred to as the reference electrode and may include one or more materials such as, e.g., silver, silver chloride, silver or silver chloride with potassium chloride (KCL), nafion, nation layers or coatings, polymer layers or coatings, polyurethane, layers or coatings, copper, copper sulfate, mercury, mercury chloride, any combination of the aforementioned materials, etc. For example, a nafion layer located on top of a silver/silver-chloride electrode may act as a protective layer to improve stability and prevent drift of the electrode potential.

The circuit portion (block 124) may include, e.g., analog and/or digital hardware and/or software, and may be electrically coupled to the sensing portion (block 122). The circuit portion (block 124) may be configured to measure one or more parameters using the sensing portion (block 122). For example, as described herein, the sensing portion (block 122) may be configured to measure a potential between two electrodes, and as such, the circuit portion (block 124) may use the sensing portion (block 122) to measure the potential between the two electrodes. In at least one embodiment, the circuit portion (block 124) includes a capacitor coupled to the electrodes that changes capacitance based on the measured potential between the two electrodes (e.g., the capacitor may be a varactor diode).

The circuit portion (block 124) may be further configured to measure a temperature proximate the sensing portion (block 122), e.g., using temperature sensitive circuitry. In at least one embodiment, the circuit portion (block 124) may include a thermistor that changes resistance based on the temperature proximate the sensing portion (block 122). In at least one embodiment, at least a portion of the temperature sensitive circuitry may also be exposed to the material (e.g., at least a portion of the temperature sensitive circuitry may be adjacent and/or in contact with the material).

Further, the circuit portion (block 124) may be shielded, or protected, from exposure to the material. For example, the circuit portion (block 124) may be encapsulated in a polymer while at least a portion of the sensing portion (block may not be encapsulated in a polymer and capable of being exposed to the material (e.g., so as to be used to measure a parameter of the material). Further, the passive sensor device (block 120) may be embedded within a container containing, or holding, the material with at least a portion of the sensing portion (block 122) exposed to the material.

Generally, the circuit portion (block 124) may be further configured to wirelessly transmit a signal representative of the measured parameter and the measured temperature when energized, e.g., by the interrogator portion (block 110). In one or more embodiments, the circuit portion (block 124) may include an inductive loop that is configured to wirelessly receive energy (e.g., from the interrogator portion (block 110) as shown by line 130) and/or wirelessly transmit a signal (e.g., to the interrogator portion (block 110) as shown by line 130) representative of the measured parameter and the measured temperature. In at least one embodiment, the circuit portion (block 124) may include an inductive loop that is electrically coupled to both a capacitor that changes capacitance based on the measured parameter and a thermistor, or temperature sensitive circuit, that changes resistance based on the temperature proximate the sensing portion (block 122). In other words, the circuit portion (block 124) may be simultaneously coupled to a capacitive sensing circuit that is configured to measure a parameter and temperature sensitive circuitry, e.g., so as to generate and transmit a single signal representative of both the measured parameter and the measured temperature.

The circuit portion (block 123) and/or the sensing portion (block 122) may be integrated, or included, on the same circuit carrier or different circuit carriers. Exemplary circuit carriers may include printed circuit boards, flexible substrates, etc. The exemplary circuits may be added to such circuit carriers using various techniques and/or technologies such as any deposition technique (e.g., thin-film deposition, etc.), any circuit printing technique (e.g., ink-jet-type printing), etc.

The circuit portion (block 124) may be configured such that the quality factor at the resonant frequency of the signal shifts in response to changes in the measured temperature proximate the sensing portion (block 122) and/or the resonant frequency of the signal shifts in response to changes in the measured parameter. In other words, the quality factor at the resonant frequency of the signal may correlate to the measured temperature proximate the sensing portion (block 122) and the resonant frequency of the signal may correlate to the measured parameter. These two values, quality factor and resonant frequency, may be extracted from the wireless transmitted signal transmitted by the circuit portion (block 124) to provide the measured temperature and the measured parameter, respectively. In other words, the measured parameter and the measured temperature may be included in a single signal.

In one or more embodiments, the circuit portion (block 124) of the passive sensor device (block 120) may be configured to wirelessly transmit the signal representative of the measured parameter and the measured temperature after a selected period of time has elapsed following the energization of the passive sensor device (block 120). In other words, the circuit portion (block 124) of the passive sensor device (block 120) may be time-gated having at least two phases that are consecutive to one another, e.g., an electrical charging or energizing phase and a signal transmitting phase. Further, in one or more embodiments, the interrogating circuitry of the interrogator portion (block 110) may be configured to wirelessly receive signals from the circuit portion (block 124) after a selected period of time has elapsed following the energization of the passive sensor device (block 120). In other words, the interrogator portion (block 110) may be time-gated having at least two phases that are consecutive to one another, e.g., an electrical charging or energizing phase and a signal receiving phase that occurs either directly or after a selected period of time after the end of the electrical charging or energizing phase.

The interrogating circuitry of the interrogator portion (block 110) may be configured to generate a temperature-compensated value of the parameter based on the signal representative of the measured parameter and the measured temperature. More specifically, e.g., the interrogating circuitry may analyze the signal from the passive sensor device (block 120) and determine the resonant frequency of the signal and the quality factor of the signal, e.g., at the resonant frequency. From the resonant frequency and the quality factor, a temperature-compensated value of the parameter may be generated. Further, the interrogating circuitry of the interrogator (block 110) may analyze the signal by determining the frequency response of the signal from the passive sensor device (block 120) and determine the resonant frequency from the peak of the response and the quality factor from the width of the response. Still further, the interrogating circuitry of the interrogator (block 110) may analyze the signal by determining the time-gated response of the signal from the passive sensor device (block 120) and determine the resonant frequency from the zero-crossings of the time response and the quality factor from the time decay of the time response.

The interrogator portion (block 110) may further include processing apparatus (block 12), which may include data storage (block 14). The processing apparatus (block 12) may be, for example, any fixed or mobile computer system (e.g., a personal computer, minicomputer, handheld computer, tablet computer, etc.). The exact configuration of the computing apparatus is not limiting and essentially any device capable of providing suitable computing capabilities and control capabilities (e.g., control the interrogator portion to interrogate the passive sensor device to acquire data, such as data related to the temperature-compensated value of a parameter) may be used. Further, various peripheral devices, such as a computer display, touchscreen, mouse, keyboard, memory, and printer, are contemplated to be used in combination with processing apparatus (block 12) of the data storage (block 14).

Figure 2:
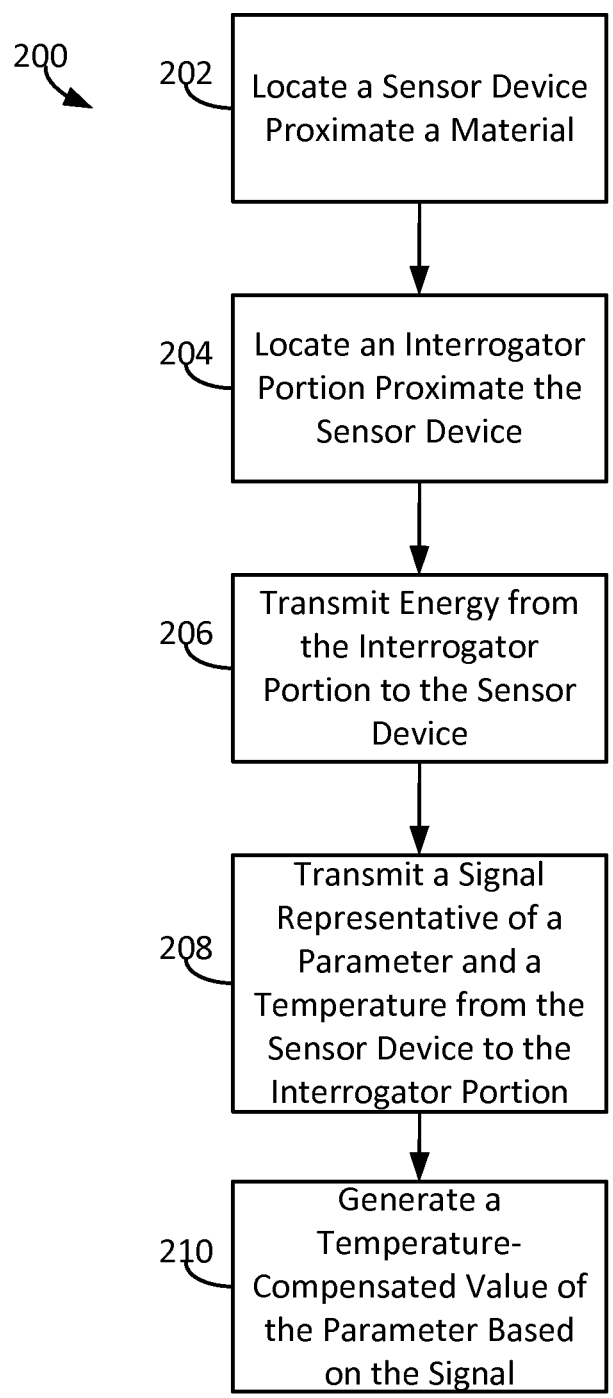
FIG. 2 depicts a general block diagram of an exemplary method for use in wireless transmission of a parameter, e.g., using the exemplary system of FIG. 1.

The data storage (block 14) may allow for access to processing programs or routines (block 16) and one or more other types of data (block 18) that may be employed to carry out the illustrative methods, e.g., at least a portion of method 200 as shown generally in the block diagram of FIG. 2. Data (block 18) may include, for example, data representative of temperature-compensated values of a parameter, data correlating resonant frequency of a signal from the passive sensor device to a parameter, data correlating quality factor of the resonant frequency of a signal from the passive sensor device to temperature, data representative of the one or more received signals, etc. The data (block 18) may further include one or more processing programs or routines employed according to the present disclosure (e.g., calculations, formulas, interrogation programs, time-gated interrogation programs, swept-frequency interrogation programs, etc.), results from one or more processing programs or routines employed according to the present disclosure (e.g., temperature-compensated values such as temperature-compensated pH values, etc.), or any other data that may be necessary for carrying out the one or more methods and processes described herein.

The exemplary methods and processes described herein may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other methods and/or processes as described herein or as would be applied in a known fashion.

The one or more programs used to implement the exemplary methods and processes described herein may be provided using any programmable language, e.g., a high level procedural and/or object orientated programming language that is suitable for communicating with a computer system. Any such programs may, for example, be stored on any suitable device, e.g., a storage media, etc., readable by a general or special purpose program running on the computer system (e.g., including processor apparatus such as a field programmable gate array, etc.) for configuring and operating the computer system when the suitable device is read for performing the methods and/or processes described herein. In other words, in at least one embodiment, the interrogator portion (block 110) may be implemented using a computer readable storage medium, configured with a computer program, where the storage medium so configured causes the computer to operate in a specific and predefined manner to perform functions described herein.

An exemplary block diagram of an illustrative method 200 of wireless transmission of one or more parameters is depicted in FIG. 2. One will recognize that one or more of the blocks of functionality described therein may be carried out using one or more programs or routines, and/or any other components of the systems and/or devices described herein. Generally, the method 200 includes locating a passive sensor device (e.g., the passive sensor device (block 120) described herein with reference to FIG. 1) proximate a material (e.g., perishable material such as food material, biological materials, biological fluids, fluids, concrete, etc.) (block 202) of which a parameter is to be measured, and locating an interrogator portion (e.g., the interrogator portion (block 110) described herein with reference to FIG. 1) proximate the passive sensor device (e.g., outside of the material) (block 204). The passive sensor device may be embedded, or a part of, packaging, or a container, for the material. For example, the passive sensor device may be embedded in the side of a milk carton or in plastic wrap of food packaging. At least a portion of the sensing portion of the passive sensor device may be exposed, e.g., in contact, with the material contained by the packaging or container such the sensing portion may be used to measure a parameter of the material contained therein. For example, if the passive sensor device is embedded in a milk carton, at least a portion of the sensing portion may be exposed to the milk inside of the milk carton.

The passive sensor device may be located in a bioreactor (e.g., flask, test tube, reactor vessel, fermentation chamber, etc.) used, e.g., to culture one or more biological materials and/or any other fluid containing apparatus. Additionally, the passive sensor device may be configured to be used with the bioreactor while the bioreactor is used in conjunction with various equipment such as, e.g., autoclaves, ovens, centrifuges, etc. to perform one or more bioprocesses. As described herein, the passive sensor device may be suspended inside the container such that material located in the container (e.g., such as biomaterial in a bioreactor) may be located between the coil of the passive sensor device and the wall of the container or located adjacent a wall of the container such as a bioreactor such that material located in the container may not be located between the coil of the passive sensor device and the wall of the container (e.g., such that the material does not interfere with the wireless transmission of signals to/from the coil of the passive sensor device). In at least one embodiment, the passive sensor device may be wedged against the side, or wall, of a bioreactor to maintain the passive sensor device adjacent the side, or wall, of the bioreactor. In at least another embodiment, the passive sensor device may be coupled to the side of the bioreactor using an innocuous material (e.g., an adhesive that does not interfere with, biologically affect, and/or chemically affect the biological material in the bioreactor).

The method 200 may further include wirelessly transmitting energy (e.g., inductively) from the interrogator portion to the passive sensor device (block 206) (e.g., to the circuit portion of the passive sensor device) and wirelessly transmitting a signal representative of a parameter and a temperature measured by the passive sensor device from the passive sensor device to the interrogator portion (block 208). In at least one embodiment, the signal representative of a measured parameter may be based on a measured potential between a first electrode exposed to the material and second electrode also exposed to the material (e.g., measured using analog and/or digital circuitry within the passive sensor device).

In one or more embodiments, the process step of wirelessly transmitting the signal representative of a measured parameter and measured temperature from the passive sensor device (block 208) occurs (e.g., after a selected period of time has elapsed) following energization of the sensor device by the wirelessly transmitted energy from the interrogator portion (block 206). In other words, wirelessly transmitting the signal representative of one or more parameters from the sensor device to the interrogator portion (block 208) may be time-gated as described herein.

The method 200 may further include generating a temperature-compensated value of the parameter based on the received signal representative of a measured parameter and measured temperature (block 210). For example, the interrogator portion may determine the resonant frequency and the quality factor of the signal, and use the resonant frequency and quality factor to generate the temperature-compensated value. In at least one embodiment, the interrogator portion may include data that correlates the resonant frequency and the quality factor to a temperature-compensated value e.g., mathematic relationships, lookup tables, algorithms, curve-fitting algorithms, correlation processes, etc.). In other words, the resonant frequency and quality factor may be inputted into a process and the output may be the temperature-compensated value. As described herein, in at least one embodiment, the temperature-compensated value is a pH value of the material.

In one or more embodiments, the signal representative of one or more parameters may be referred to as an "output" of the method 200. The "output" (e.g., one or more signals, one or more values, a digital file, a file in user-readable format, etc.) of the systems, devices, and/or methods described herein may be analyzed by a user, used by another machine that provides output based thereon, etc.

Figure 3:
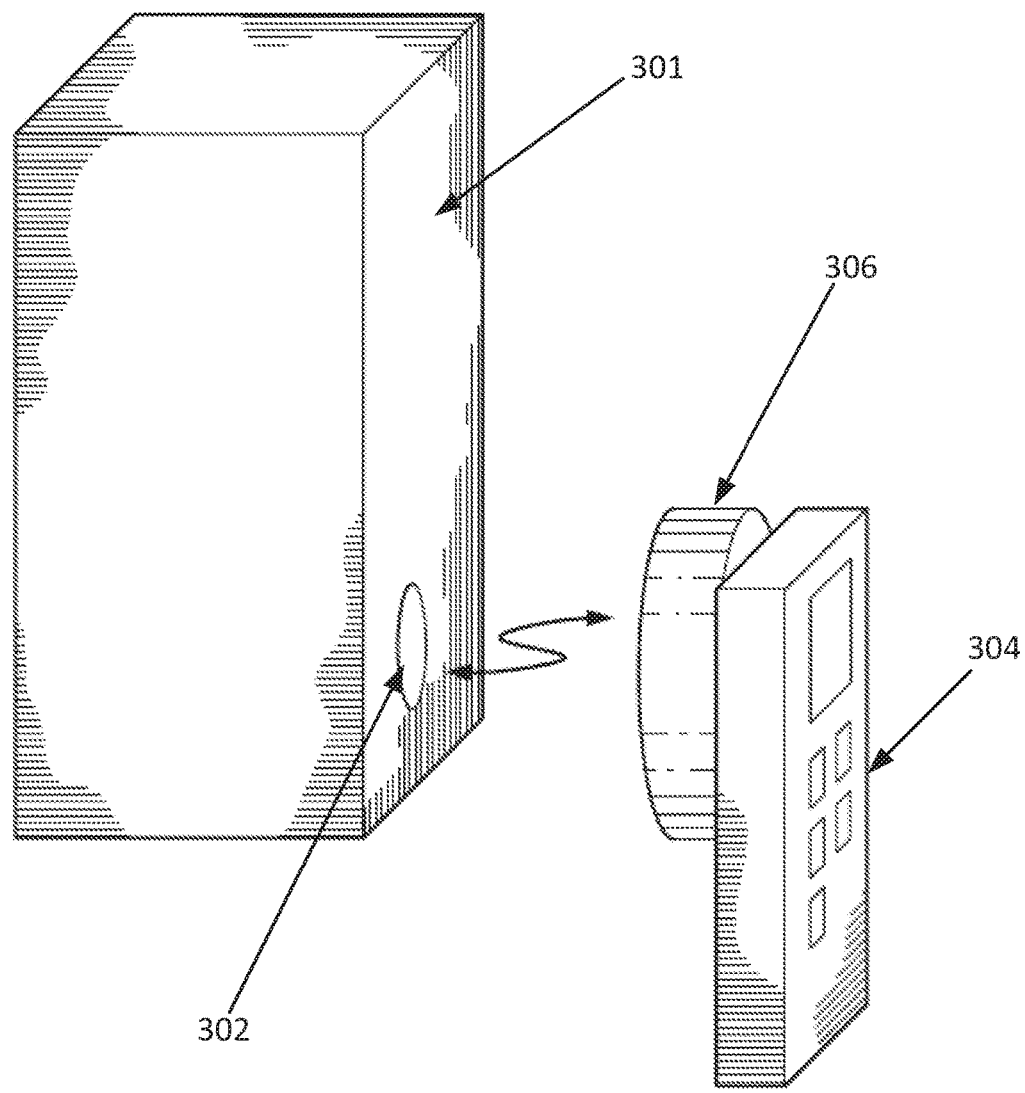
FIG. 3 is a graphical depiction of the exemplary system of FIG. 1.

An exemplary passive sensor device 302 located proximate a material within a container 301 is depicted in FIG. 3. For example, the passive sensor device 302 may be at least partially embedded within a wall of the container 301 such that the sensing portion of the passive sensor device 302 may be exposed to the material located within the container 301. An interrogator device 304 may be located proximate the passive sensor device 302 to deliver energy through induction using an inductive loop 306 to the passive sensor device 302. Once energized, the passive sensor device 302 may transmit a signal representative of a measured parameter of the material within the container 301 and a measured temperature proximate the sensing portion or of the material itself using an inductive loop. After the interrogator device 304 has received the signal, the interrogator device 304 may then generate a temperature-compensated value of the parameter of the material within the container 301 based on the signal.

Figure 4A:
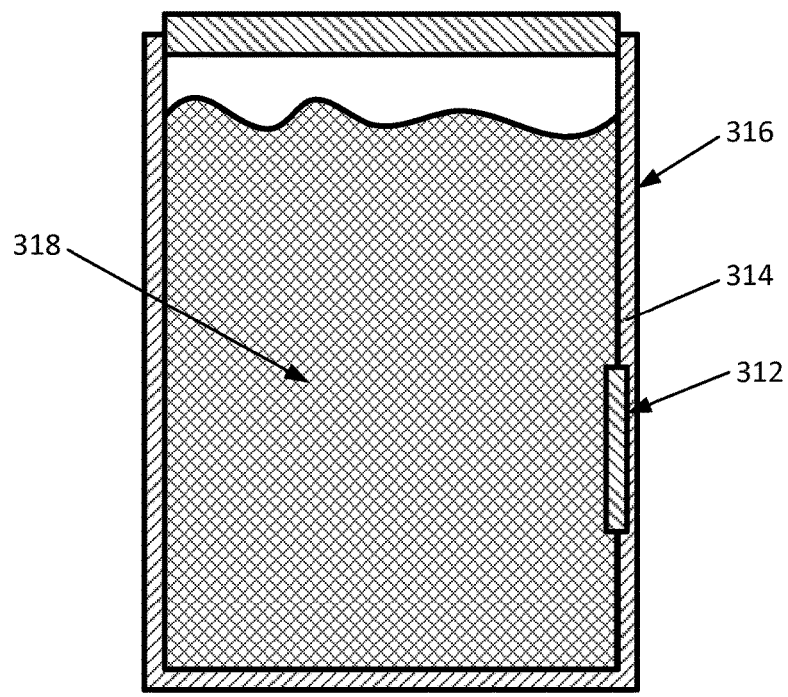
FIGS. 4A-B are cross-sectional views of the exemplary system of FIG. 1 used within a container holding fluid material.

Another exemplary passive sensor device 312 partially-embedded in the wall 314 of a fluid-holding container 316 is depicted in FIG. 4A. As shown, at least a portion of the passive sensor device 312 may be exposed to the fluid 318 contained, or held within, the fluid-holding container 316. As described herein, the fluid-holding container may be any container configured to hold a fluid. In at least one embodiment, the fluid-holding container 316 may be a milk carton, or any other container 316 configured to hold a perishable fluid. In at least another embodiment, the fluid-holding container 316 may be a bioreactor (e.g., a test tube, a flask, etc.) configured to be used in bioprocesses (e.g., cultivating cells, etc.). The circuitry, or circuit portion, of the passive sensor device 312 may be hermetically-sealed from moisture ingress of the fluid 318. For example, the circuitry may be contained, or encapsulated, in a polymer. In at least one embodiment, the material that the circuitry is contained within may be a low-loss material to, e.g., permit the wireless transmission of signals to/from the passive sensor device 312.

Further, the container, or encapsulation, may define a sealed cavity within which the circuitry of the passive sensor portion 312 resides. In at least one embodiment, the container may define at least two portions that may be coupled to each other around the passive sensor portion 312 to hermetically seal the circuitry of the passive sensor portion 312. Further, the container may define one or passages therethrough that at least a portion of the sensing portion such as the electrodes (not shown in FIG. 4A) of the passive sensor portion 312 may extend through such that may be exposed to the fluid 318.

Figure 4B:
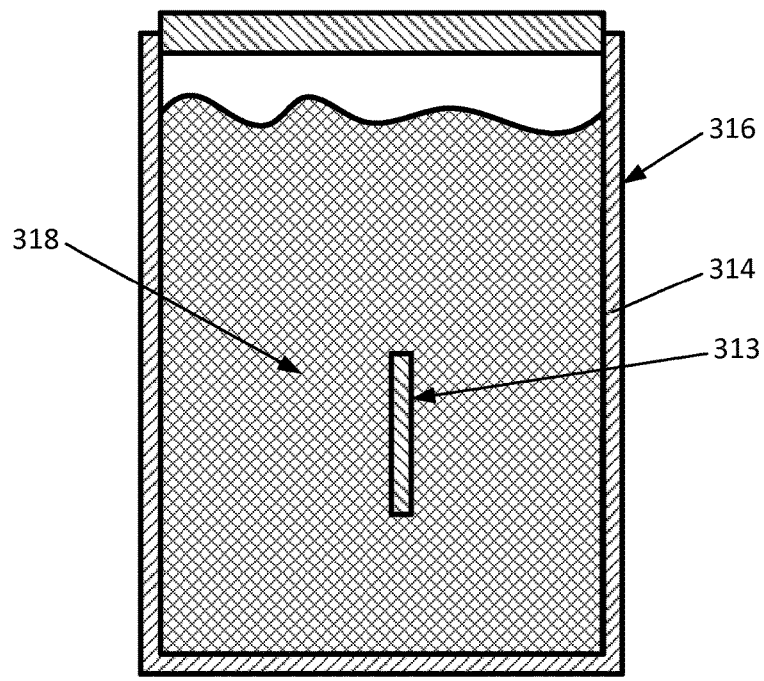

An exemplary passive sensor device 313 is shown in FIG. 4B located within the middle of the fluid within the fluid-holding container 316. Although not depicted, the passive sensor device 313 may be suspended, or held, by one or more structures and/or apparatus to maintain the sensor device 313 located within the fluid (e.g., completely surrounded by the fluid, etc.). The passive sensor device 313 may be located in the fluid (e.g., a distance from a wall of the container, etc.) such that an energizing signal from an interrogator may be received and that an data signal (e.g., including parameter measurement data) may be transmitted from the sensor through the fluid between sensor and wall of the container, e.g., without a loss in quality (e.g., such that the sensor may be energize, such that the data received by the interrogator has sufficient quality to determine data therefrom, such that the signal-to-noise ratio is sufficient, etc.

Figure 5:
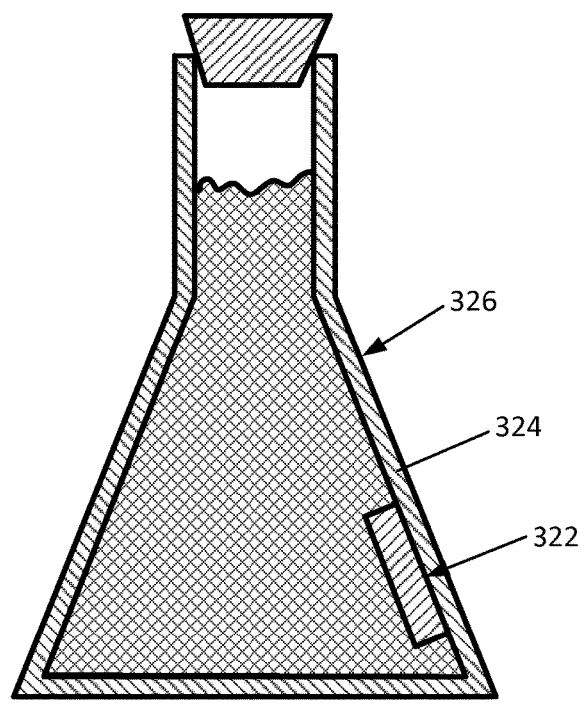
FIG. 5 is a cross-sectional view of the exemplary system of FIG. 1 used within a flask holding fluid material.

Another exemplary passive sensor device 322 adjacent a wall 324 of a fluid-holding container 326 is depicted in FIG. 5. As shown, the container 326 is a flask such as those used in bioreactors and/or any other bioprocesses. The passive sensor device 322 may be removably coupled to the wall 324 of the container 326. Further, in at least one embodiment, the passive sensor device 322 may be weighted (e.g., mass increase to keep the passive sensor device 322 below the surface of a fluid material (e.g., to maintain contact between the sensing portion and the fluid material, to locate the device at the bottom of the container for interrogation from underneath the container, etc.).

EXAMPLES

Wireless Passive Sensor for Temperature Compensated Remote pH Monitoring

As described herein, accurate measurement of pH with electrode-based wireless passive sensors may be affected by temperature, and as a result, electrode-based wireless passive sensors may not be suitable for measuring pH when the temperature of the solution varies over a wide range. For example, an increase in a solution's temperature may cause a decrease in viscosity and an increase in the mobility of its ions in the solution. Further, for example, an increase in temperature may also increase the number of ions in the solution due to the dissociation of molecules (e.g., for weak acids and bases). As pH is a measure of the hydrogen ion concentration, a change in the temperature of a solution may result in a change of pH. Since this is not an error, there is no need to correct or compensate for this temperature effect.

The Nernst equation describes the effect of temperature on the pH combination electrode's response (or sensitivity) to pH (see, e.g., A. A. Panova, P. Pantano, D. R. Walt, "in situ fluorescence imaging of localized corrosion with a pH sensitive imaging fiber," *Anal. Chem.*, vol. 69, no. 8, pp. 1635-1641, April 1997; and P. Kurzweil, "Metal oxides and ion-exchanging surfaces as pH sensors in liquids: state-of-the-art and outlook," *Sensors*, vol. 9, pp. 4955-4985, 2009).

The temperature sensitivity of an exemplary combination electrode may increase when the solution's pH is further from the isothermal point. For accurate measurement of pH, the change of sensitivity may be compensated by measuring pH and temperature of the solution simultaneously.

An exemplary integrated wireless passive pH and temperature sensor for temperature compensated remote pH monitoring is described in this example. The sensor may include a passive RLC resonator whose resonant frequency and quality factor change with the pH and temperature of the solution, respectively. Changes in the sensor's resonant frequency and quality factor may be detected by measuring the induced change in the impedance of an external interrogator coil that may be inductively coupled to the sensor inductor.

Experimental results of the exemplary sensor operating from a pH of 1.5 to a pH of 12 and from 25 degrees Celsius (° C.) to 55° C. are further described in this example. Simultaneous measurements of pH and temperature of the solution may be used for employing temperature compensation in pH measurement, and thus, the exemplary sensor may overcome the pH measurement error due to temperature dependence of the electrode.

Figure 6:
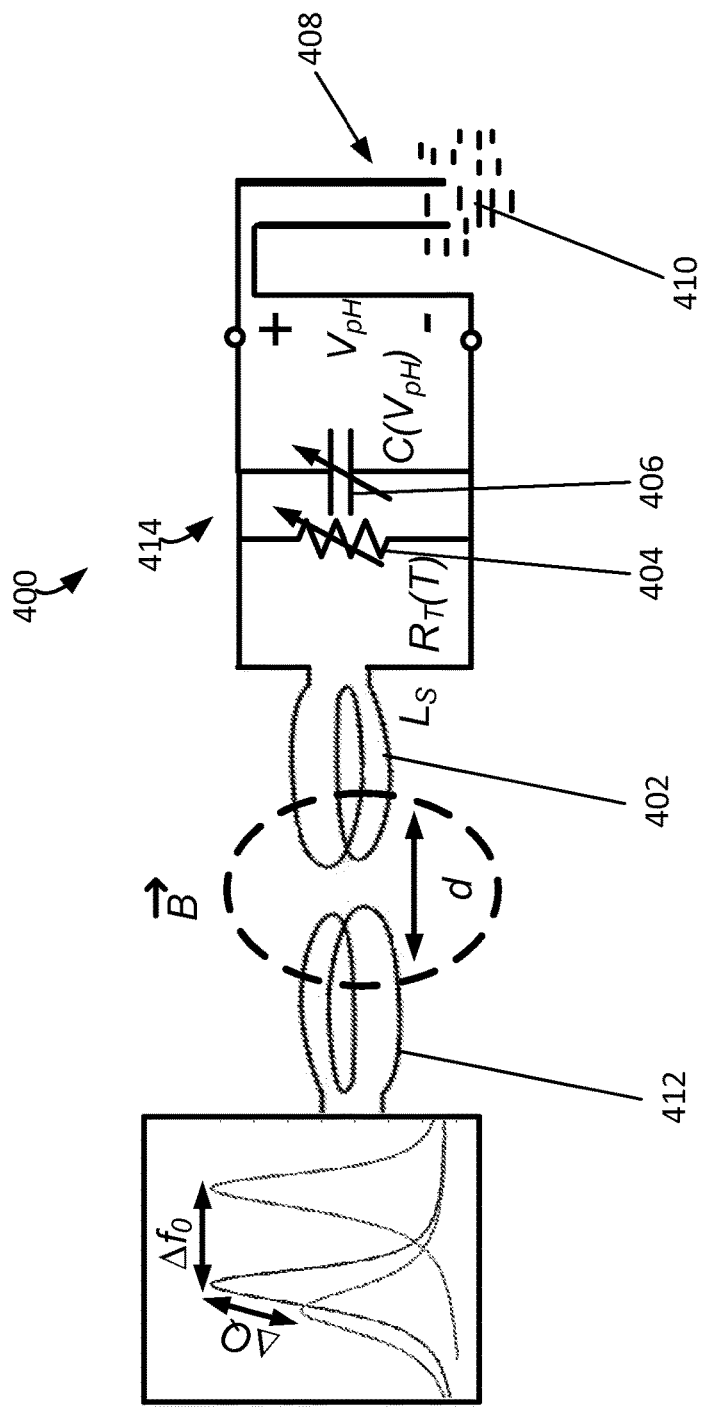
FIG. 6 is a conceptual diagram of an exemplary system for use in wireless passive transmission of pH and temperature.

A block diagram of the wireless passive pH and temperature sensor 400 is shown in FIG. 6. In the remote sensor 400, a spiral inductor 402 is connected in parallel with a temperature dependent resistor (thermistor) 404 and a voltage dependent capacitor 406 (e.g., varactor) based voltage sensing circuit 414. A pH combination electrode 408 is connected in parallel with the voltage dependent capacitor 406 and provides a biasing voltage to the voltage dependent capacitor 406. The pH combination electrode 408 may include an iridium/iridium oxide sensing electrode and a silver/silver chloride reference electrode. An iridium/iridium oxide electrode may have the advantages of easy preparation, small size, continuous detection, fast and stable response in aqueous, non-aqueous, non-conductive, and even corrosive media, a linear response to pH with reference to a silver/silver chloride electrode from a pH of 2 to a pH of 12, low impedance, no requirement for pretreatment and negligible interference of ions and complexing agents. Such pH combination electrodes maybe used in technical media, such as fuels, food applications, and biological media (see, e.g., W. D. Huang, S. Deb, Y. S. Seo, S. Rao, M. Chiao and J. C. Chiao, "A passive radio-frequency pH-sensing tag for wireless food-quality monitoring," *IEEE Sensors J.*, available through IEEE early access; G. Papeschi, S. Bordi, M. Carlagrave, L. Criscione and F. Ledda, "An iridium-iridium oxide electrode for in vivo monitoring of blood pH changes," *Journal of Medical Engineering & Technology*, vol. 5, no. 2, pp. 86-88, March 1981; P. Kurzweil, "Metal oxides and ion-exchanging surfaces as pH sensors in liquids: state-of-the-art and outlook," *Sensors*, vol. 9, pp. 4955-4985, 2009; and S. Yao, M. Wang and M. Madou, "A pH electrode based on melt-oxidized iridium oxide," *Journal of the electrochemical society*, vol. 148, no. 4, pp. 29-36, 2001).

In the sensor 400 shown in FIG. 6. $L_S$ is the inductance of the spiral inductor 402, $R_T(T)$ is the temperature dependent resistance, T is the temperature of the contact solution 410, $C(V_{pH})$ is the capacitance of the voltage sensing circuit 414, and $V_{pH}$ is the potential difference developed at the pH combination electrode 408 when in contact with a solution 410. The capacitance, $C(V_{pH})$ changes in response to the low frequency change of the biasing voltage, $V_{pH}$ while variation of temperature, T varies the resistance, $R_T(T)$. The spiral inductor 402, resistor 404, and capacitor 406 form a resonant circuit with a resonant frequency, $f_0$, and a quality factor, Q, given by (with no magnetic coupling) (see, e.g., K. Zeng, K. G. Ong, C. Mungle and C. A. Grimes, "Time domain characterization of oscillating sensors: Application of frequency counting to resonance frequency determination," *Review of Scientific Instruments*, vol. 73, no. 12, pp. 4375-4380, December 2002).

$$f_0 = \sqrt{1 - \frac{1}{4Q^2}} \times \frac{1}{2\pi\sqrt{L_S C(V_{pH})}}. \quad (2)$$

$$Q \cong R_T(T)\sqrt{\frac{C(V_{pH})}{L_S}}. \quad (3)$$

An interrogator coil 412 may be inductively coupled to the sensor inductor coil 402 and may be used to track the resonant frequency and quality factor of the sensor. In this manner, the measured resonant frequency and quality factor are directly related to the potential difference developed at the pH combination electrode 408 and temperature of the solution 410, respectively.

Figure 7:
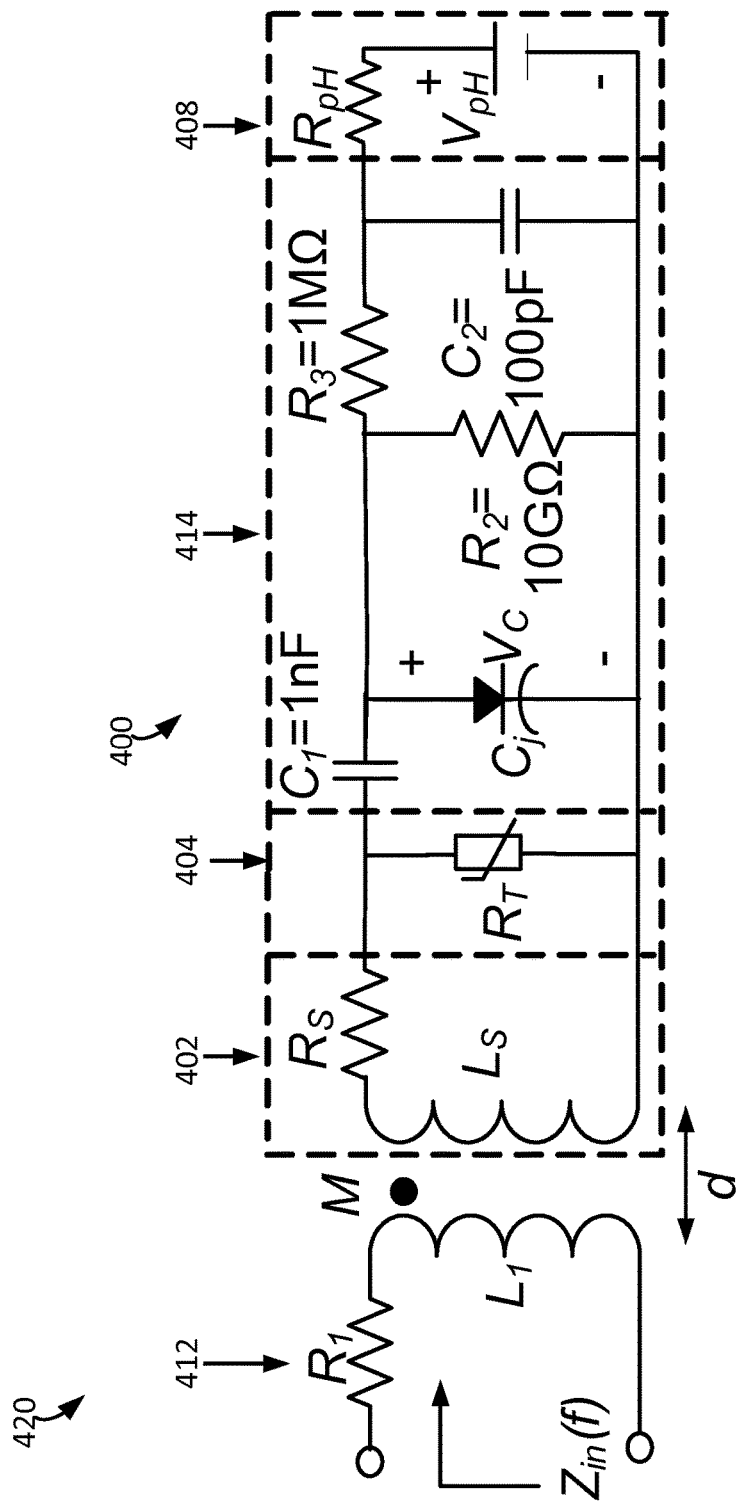
FIG. 7 is an exemplary circuit diagram of the system of FIG. 6.

An equivalent circuit diagram 420 of the fabricated wireless passive temperature and pH sensor is shown in FIG. 7. In the circuit, $L_S$ and $R_S$ are the series inductance and resistance of the sensor inductor 402, respectively, and $L_1$ and $R_1$ are the series inductance and resistance of the interrogator coil 412, respectively. M is the interrogator-sensor inductive coupling factor. $R_T$ is the resistance of the temperature dependent resistor (thermistor), which decreases with increasing temperature. $C_j$ is the small signal junction capacitance of the voltage dependent capacitor 406 (e.g., varactor diode) in the voltage sensing circuit 414. In the reverse bias state, $C_j$ is approximated by $C_j(V_C)=C_0(1-V_C/\phi)^{-\gamma}$, where $C_0$ is the junction capacitance at zero bias, $\phi$ is the junction built-in potential, $\gamma$ is the doping dependent exponent, and $V_C$ is the bias voltage applied across the varactor 406. The temperature dependence of $C_j$ may be ignored. $V_{pH}$ and $R_{pH}$ are the potential difference and the cell resistance, respectively, developed at the pH combination electrode 408 when in contact with a solution 410. In the circuit 420, $R_3$ and $C_2$ act as a low pass filter so that the resonator may be insensitive to the loading of the electrode cell by $R_{pH}$ and the varactor 406 may respond to low frequency variations in $V_{pH}$. For a small interrogator source oscillation amplitude, small M, and $R_{pH}<<(R_2+R_3)$, $V_C \cong V_{pH}$. As $C_1>>C_j(V_C)$, the following may be approximated: $C(V_{pH}) \sim C_j(V_{pH})$. The pH of the contact solution 410, which is indicated by $V_{pH}$, and temperature of the solution 410, T, can then be monitored by tracking the resonant frequency and quality factor of the sensor 400, respectively (see, e.g., K. Zeng, K. G. Ong, C. Mungle and C. A. Grimes, "Time domain characterization of oscillating sensors: Application of frequency counting to resonance frequency determination," *Review of Scientific Instruments*, vol. 73, no. 12, pp. 4375-4380, December 2002).

Referring to FIG. 7, near and at resonant frequency of the sensor the impedance, $Z_{in}$, may be given as:

$$Z_{in}(f) = Z_1 + Z_T = R_1 + j2\pi f L_1 + \frac{(2\pi f)^2 M^2}{Z_S}, \quad (4)$$

where f is the interrogator source frequency and $Z_S \cong R_S + j2\pi f L_S + (R_T/(1+j2\pi f C R_T))$, is the sensor series impedance. In the exemplary system, the resonant frequency and quality factor were obtained from the real part of the impedance, $Z_{in}$, using a quadratic curve-fitting algorithm (see, e.g., R. Nopper, R. Niekrawietz and L. Reindl, "Wireless readout of passive LC sensors," *IEEE Transaction on instrumentation and Measurement*, vol. 59, no. 9, pp. 2450-2457, September 2010; and M. P. Robinson and J. Clegg, "Improved determination of Q-factor and resonant frequency by a quadratic curve fitting method," *IEEE Transaction on Electromagnetic Compatibility*, vol. 47, no. 2, pp. 399-402, May 2005).

The impedance, $Z_{in}$, in equation (4) consists of two components: $Z_1=R_1+j2\pi f L_1$, due to the self-impedance of the interrogator coil 412; and $Z_T=(2\pi f)^2 M^2/Z_S$, due to the sensor coupling. To remove the self-impedance of the interrogator coil 412, a background subtraction, using the measured impedance of the interrogator coil 412 when the sensor 400 was absent, was implemented prior to measuring the sensor response (see, e.g., J. B. Ong, Z. You, J. Mills-Beale, E. L. Tan, B. D. Pereles and K. G. Ong, "A wireless, passive embedded sensor for real time monitoring of water content in civil engineering materials," *IEEE Sensors J.*, vol. 8, issue 12, pp. 2053-2058, December 2008).

Figure 8:
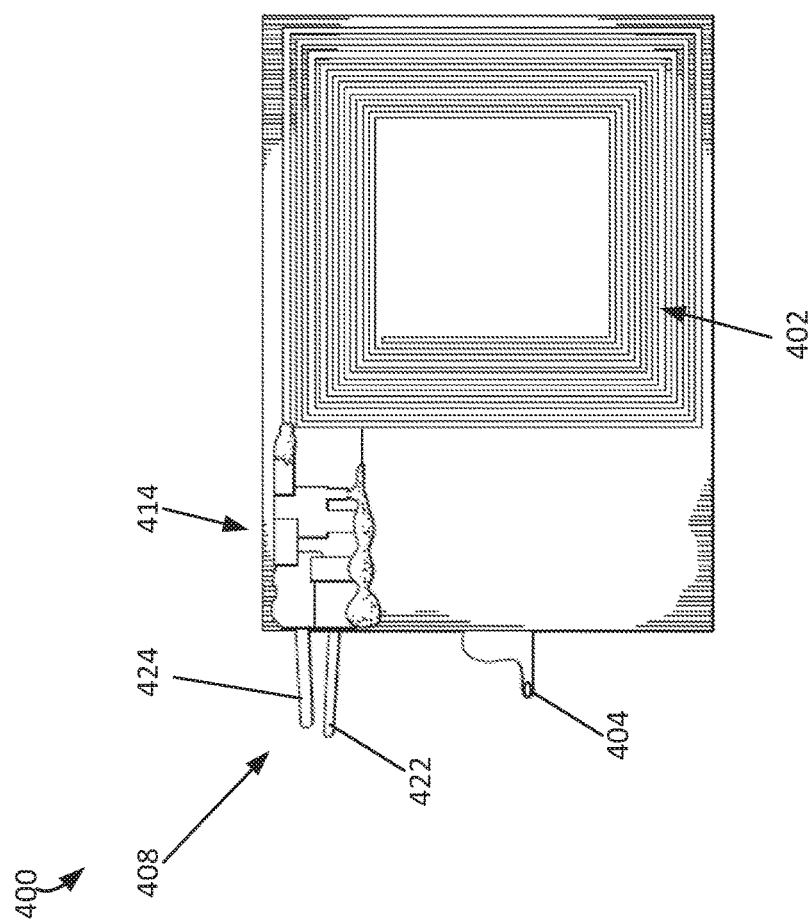
FIG. 8 is a photograph of an exemplary sensor for use in the system of FIG. 6.

The iridium/iridium oxide (Ir/IrO$_x$) sensing electrode 422 as shown in FIG. 8 was prepared by direct oxidation method. Ir metal wire (e.g., 0.5 mm in diameter, 99.8% purity, obtained from Alfa AESAR) of about 10 mm in length was ultrasonically cleaned with 6 molar (M) Hydrogen Chloride (HCl) solution followed with de-ionized water. The clean wire was then oxidized by bringing it to a temperature of 800° C. in an electric oven for 45 minutes after wetting its surface with 1 M sodium hydroxide (NaOH) solution. The wetting and heating process was repeated six times until a blue-black coating was formed on the surface (see, e.g., G. Papeschi, S. Bordi, M. Carlagrave, L. Criscione and F. Ledda, "An iridium-iridium oxide electrode for in vivo monitoring of blood pH changes." *Journal of Medical Engineering & Technology*, vol. 5, no. 2, pp. 86-88, March 1981; and R. A. Macur, "Iridium-iridiumoxide electrode for measuring pH of blood and other fluids," U.S. Pat. No. 3,726,777, Apr. 10, 1973).

Further, the electrode 422 was immersed in boiling deionized (DI) water for an hour, and then immersed in DI water at room temperature for 30 days to reduce aging effects (see, e.g., R.-G. Du, R.-G. Hu, R.-S. Huang and C.-S. Lin, "In situ measurement of Cl— concentrations and pH at the reinforcing steel/concrete interface by combination sensors," *Anal. Chem.*, vol. 78, no. 9, pp. 3179-3185, March 2006; and S. Yao, M. Wang and M. Madou, "A pH electrode based on melt-oxidized iridium oxide," *Journal of the electrochemical society*, vol. 148, no. 4, pp. 29-36, 2001). A small area of (e.g., about 2 mm in length) iridium oxide film at one end was removed (e.g., scraped off) the electrode 422 and was connected to an insulated wire using silver epoxy. Further, silicone sealant (e.g., GE Silicone I) was applied over the connection area for electric insulation.

The silver/silver chloride (Ag/AgCl) reference electrode 424 (e.g., obtained from DOCXS biomedical products and accessories) as show in FIG. 8 was 0.5 mm in diameter and 8 mm in length. Soft silver wire was attached to the electrode for electrical connection. An insulated wire was connected to the silver wire and the connection area was electrically insulated with silicone sealant.

The sensor 400, as shown in FIG. 8, was constructed using the Ir/IrO$_x$ electrode 422 and Ag/AgCl electrode 424. The sensor 400 was designed to have a resonant frequency, f$_0$, near 18 Megahertz (MHz). Further, the sensor inductor 402 and the voltage/temperature sensing circuit 414 were fabricated on a 4 centimeter (cm)×3 cm single sided FR4 printed circuit board (PCB) with surface mount capacitors and resistors. The inner and outer dimensions of the square, eight-turn planar spiral inductor were 1.45 cm and 2.68 cm, respectively, producing L$_S$=2.1 microhenries (μH) and R$_S$=2.2 ohm (Ω) at 18 MHz. The resistance of the thermistor 404 (e.g., Honeywell 112-105PAJ-B01), R$_T$, varied from 0.015 MΩ to 0.008 MΩ at 18 MHz for temperatures from 25° C. to 55° C., respectively. The junction capacitance of the varactor 406 (e.g., NXP BB202) used in the voltage sensing circuit, C$_j$, varied from 35.04 picofarads (pF) to 22.95 pF for reverse bias voltages from 0 volt (V) to 1V, respectively. The electrode resistance, R$_{pH}$, for pH solutions in from a pH of 1.5 to a pH of 12 was approximately 3.16 megaohms (MΩ). The Ag/AgCl and Ir/IrO$_x$ electrodes 424, 422 were connected to the positive and negative terminals of the voltage sensing circuit 414, respectively.

The interrogator coil 412 was 5.1 cm in diameter and constructed of 5 turns of insulated copper wire of 1.2 mm diameter, producing L$_1$=2.35 μH, R$_1$=334.13 milliohms (mΩ) and a self-resonant frequency, f$_{res}$=28.32 MHz. The resonant frequency and quality factor of the sensor 400 were determined by measuring the real part of the impedance of the interrogator coil 412, Re{Z$_{in}$}, when inductively coupled to the sensor coil 402. The interrogator coil 412 impedance was measured using an impedance analyzer 442 (e.g., Agent 4294A) with the voltage oscillation level of the analyzer set to 25 millivolts (MV).

For all tests, solutions of different pH were made by adding 0.01M NaOH to 0.03M nitric acid (HNO$_3$). During the tests, the pH and temperature of the solutions were continuously monitored using a commercial pH-meter with automatic temperature compensation (e.g., PH150-C-ExS-tik) and a thermometer, respectively.

Figure 9:
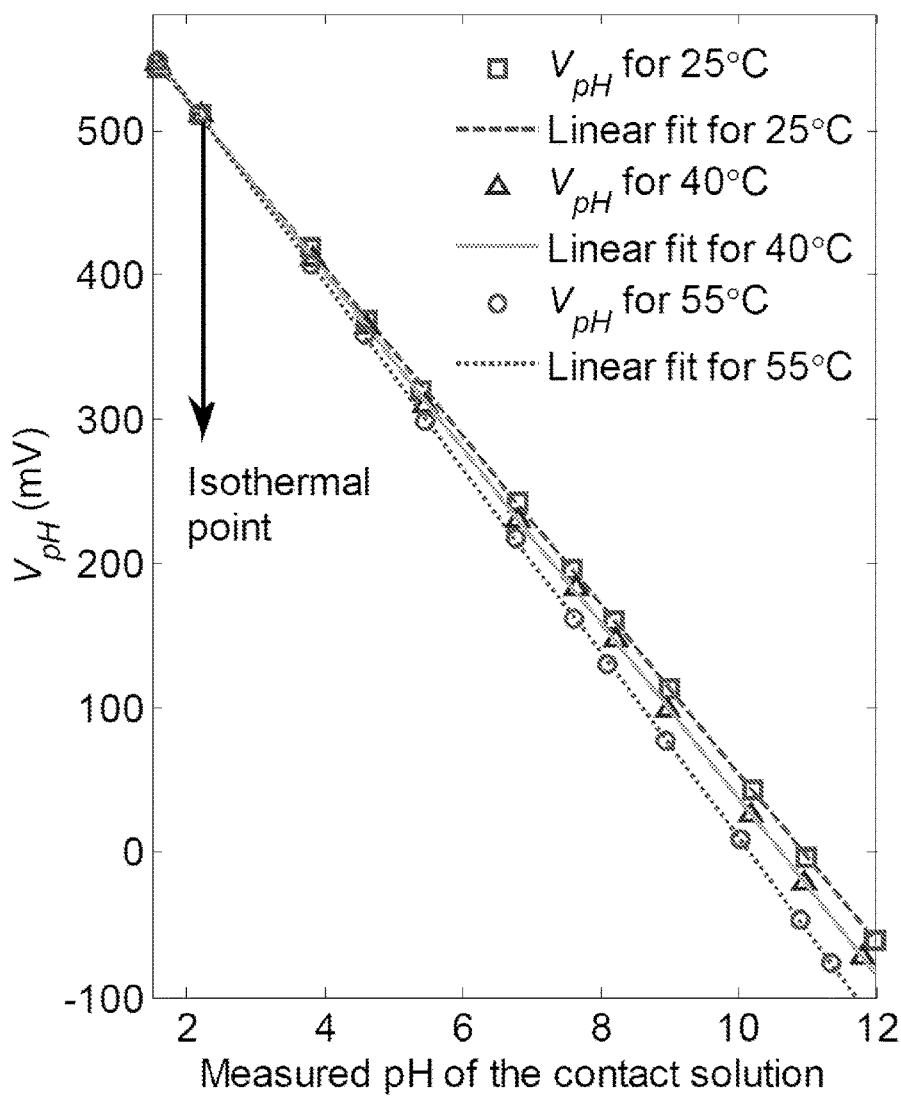
FIG. 9 is a graph of the potential difference of a pH combination electrode of the system of FIG. 6 versus pH of a contact solution for different solution temperatures.

The potential difference between the sensing and reference electrodes 422, 424, V$_{pH}$, was measured as a function of pH of the test solutions using a high impedance digital multimeter (e.g., Agent 3314A). Each solution was heated from 25° C. to 55° C. FIG. 9 shows that at a fixed temperature V$_{pH}$ has a linear response to pH. The slope was −58.19 mV/pH at 25° C. which was very close to the Nernstian slope (−59.16 mV/pH at 25° C.). Further, the slope increases with temperature. The linear fits for three different temperatures, namely, 25° C., 40° C. and 55° C., were used to determine the isothermal point, which was 2.2 pH for the pH combination electrode 408.

Figure 10:
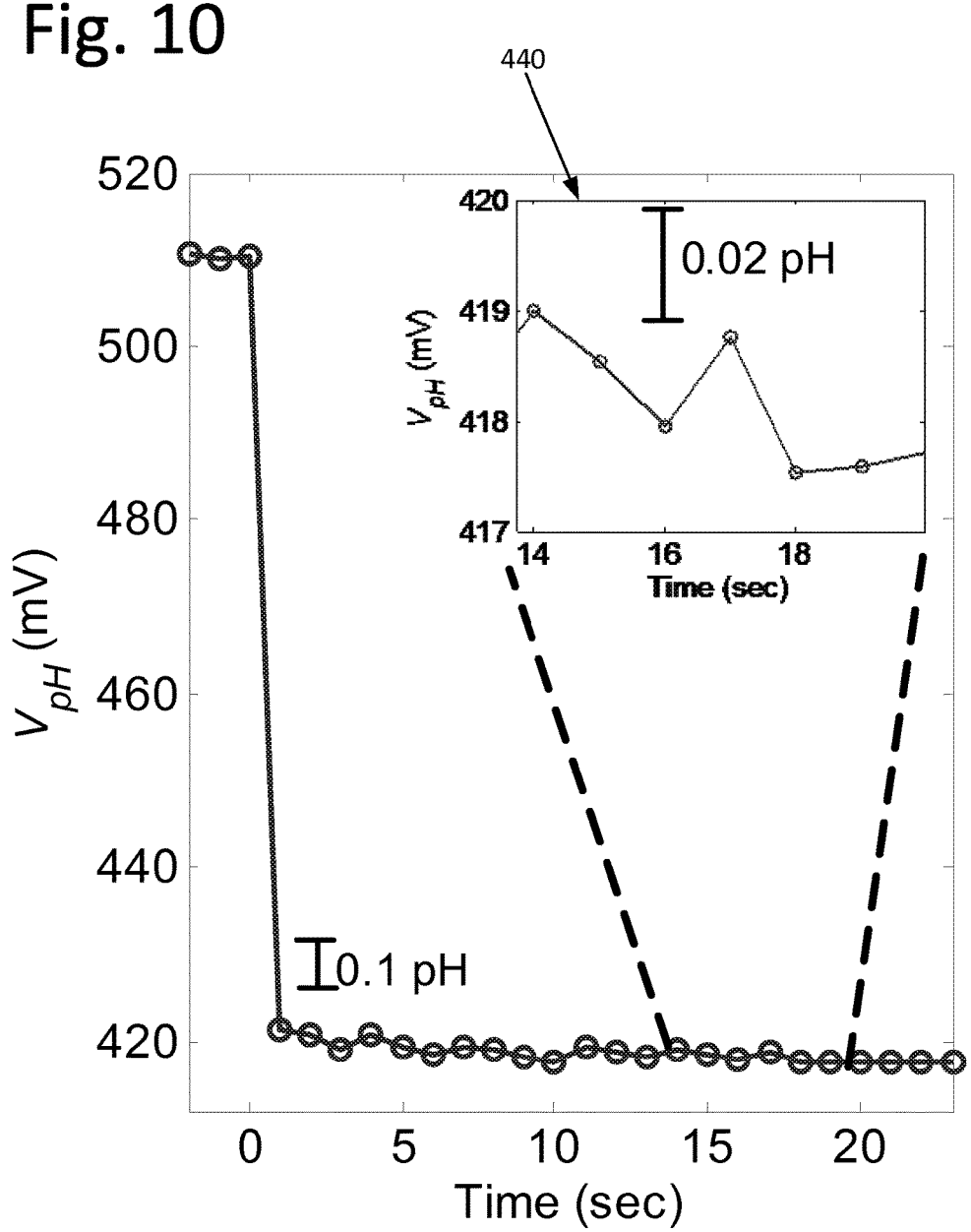
FIG. 10 is a graph of electrode potential difference response to a step change in solution pH (from a pH of 2.2 to a pH of 3.8) at a temperature of 23±0.3° C. using the system of FIG. 6.

To investigate the response time of the pH combination electrode 408, a rapid step change in the pH of the test solution was performed by quickly adding NaOH to the test solution. The test was carried out at a room temperature of 23±0.3° C. The solution was stirred vigorously during the test. The dynamic response is shown in FIG. 10. For a step change of 1.6 pH, the response of the pH combination electrode 408 is less than 1 second for an accuracy of 0.1 pH. The small changes in the V$_{pH}$ values after 1 second (see insert 440 of FIG. 10) may result from the solution mixing.

Figure 11:
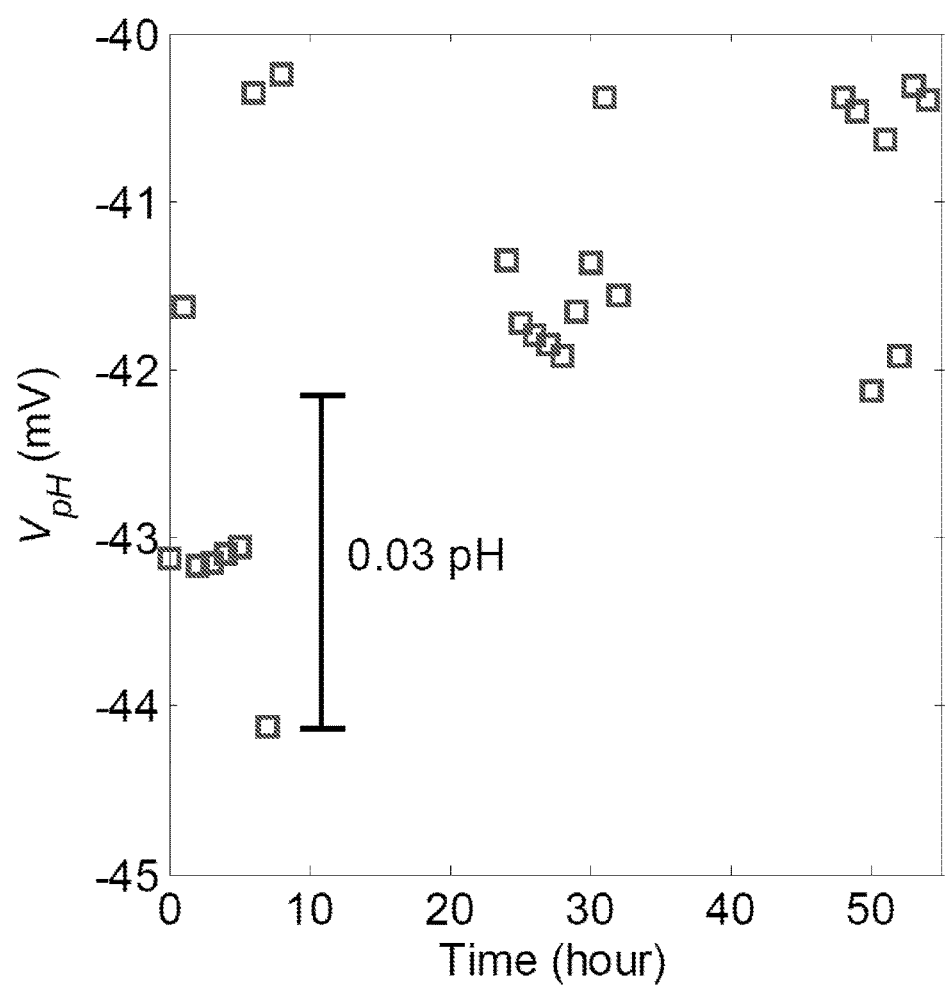
FIG. 11 is a graph of stability of an exemplary pH combination electrode of the system of FIG. 6 in a 11.65 pH solution at a temperature 24±1° C.

Drift of the electrode potential difference, V$_{pH}$, over time could cause error in pH measurements that cannot be eliminated by calibration. A two day long test was performed to identify the stability of, V$_{pH}$, with time. FIG. 11 shows V$_{pH}$ of the combination electrode 408 monitored for a solution having a pH of 11.65 over 54 hours at a temperature of 24° C. The value of V$_{pH}$ was almost constant, centered at 42.25 mV, with a deviation of less than ±2 mV (±0.03 pH) over the 54 hour period, which may indicate that the pH combination electrode 408 has high stability (e.g., which may make it suitable for continuous measurement without frequent calibration). The small deviation over time may be the variation in room temperature (±1° C.) as pH of the solution is temperature dependent. The variation of the pH of the solution, as measured by the commercial pH meter, was ±0.02 pH.

Figure 12:
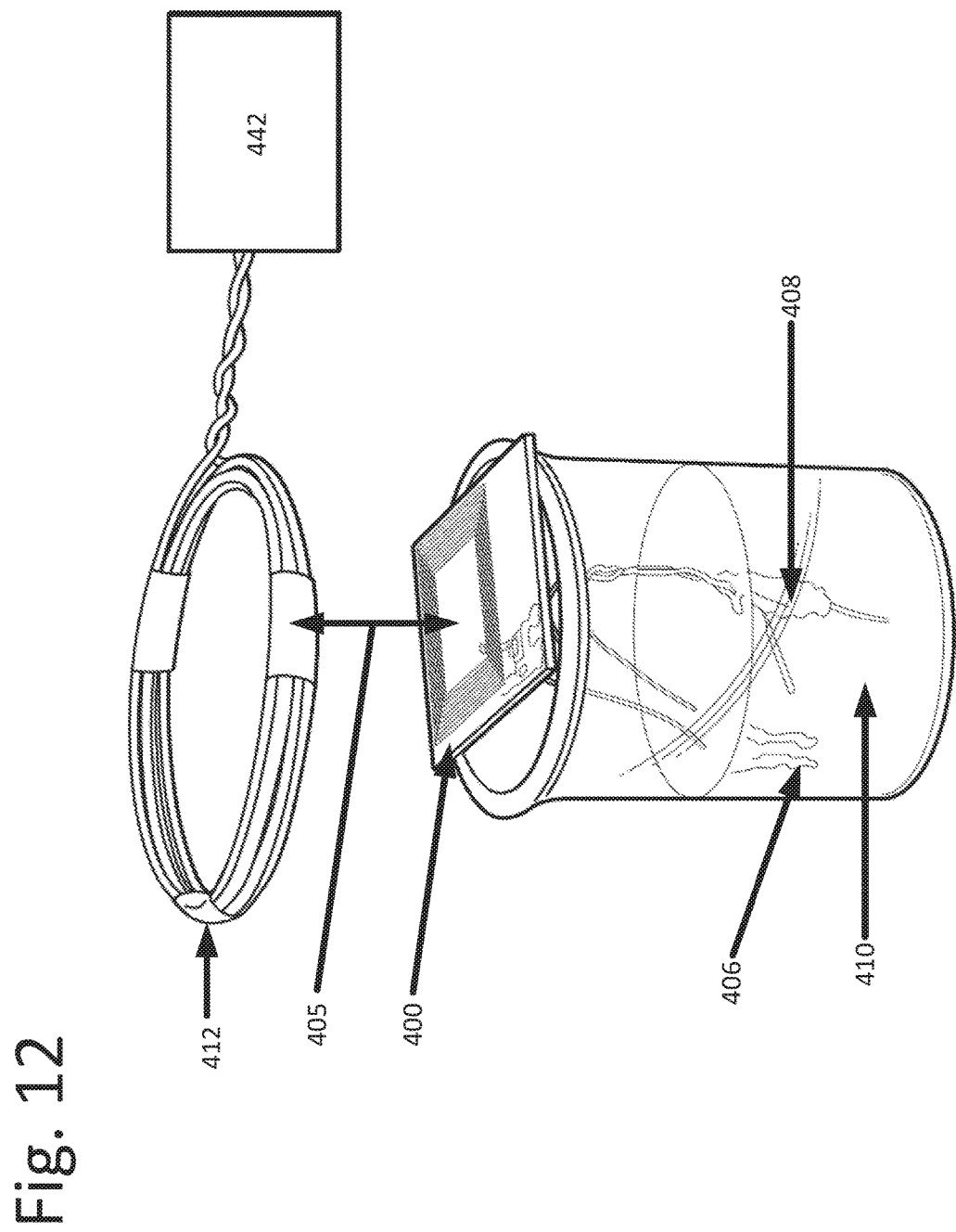
FIG. 12 is photograph of an experimental setup using the system of FIG. 6.
Figure 13:
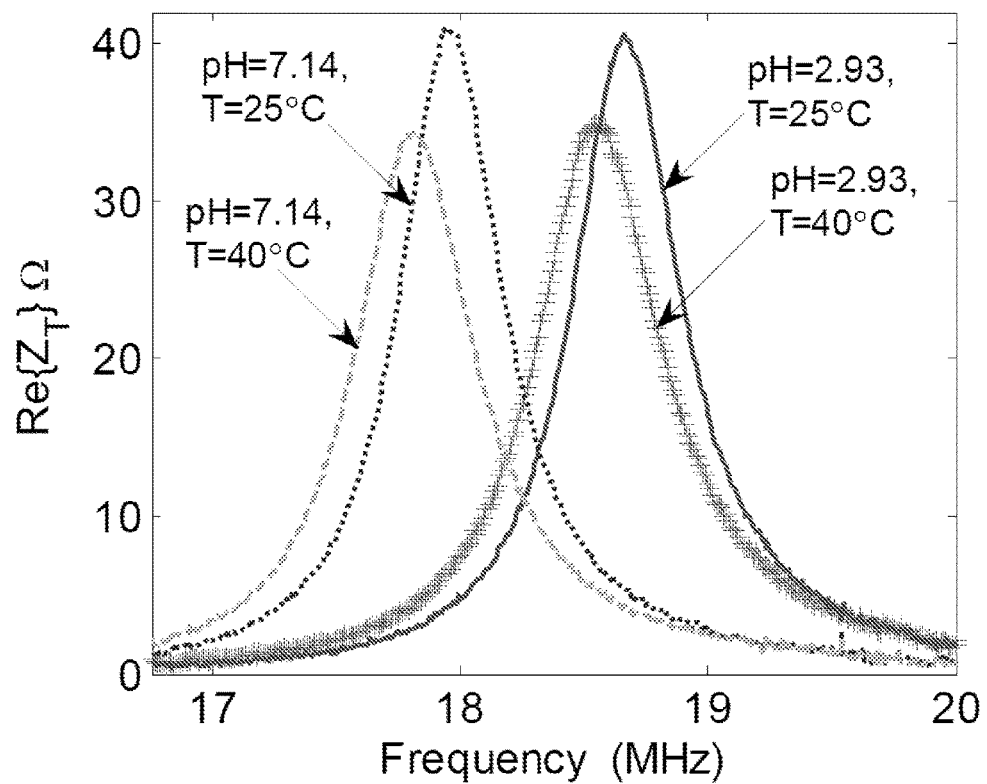
FIG. 13 is a graph of frequency response of an exemplary sensor of the system of FIG. 6 at different operating conditions.
Figure 14:
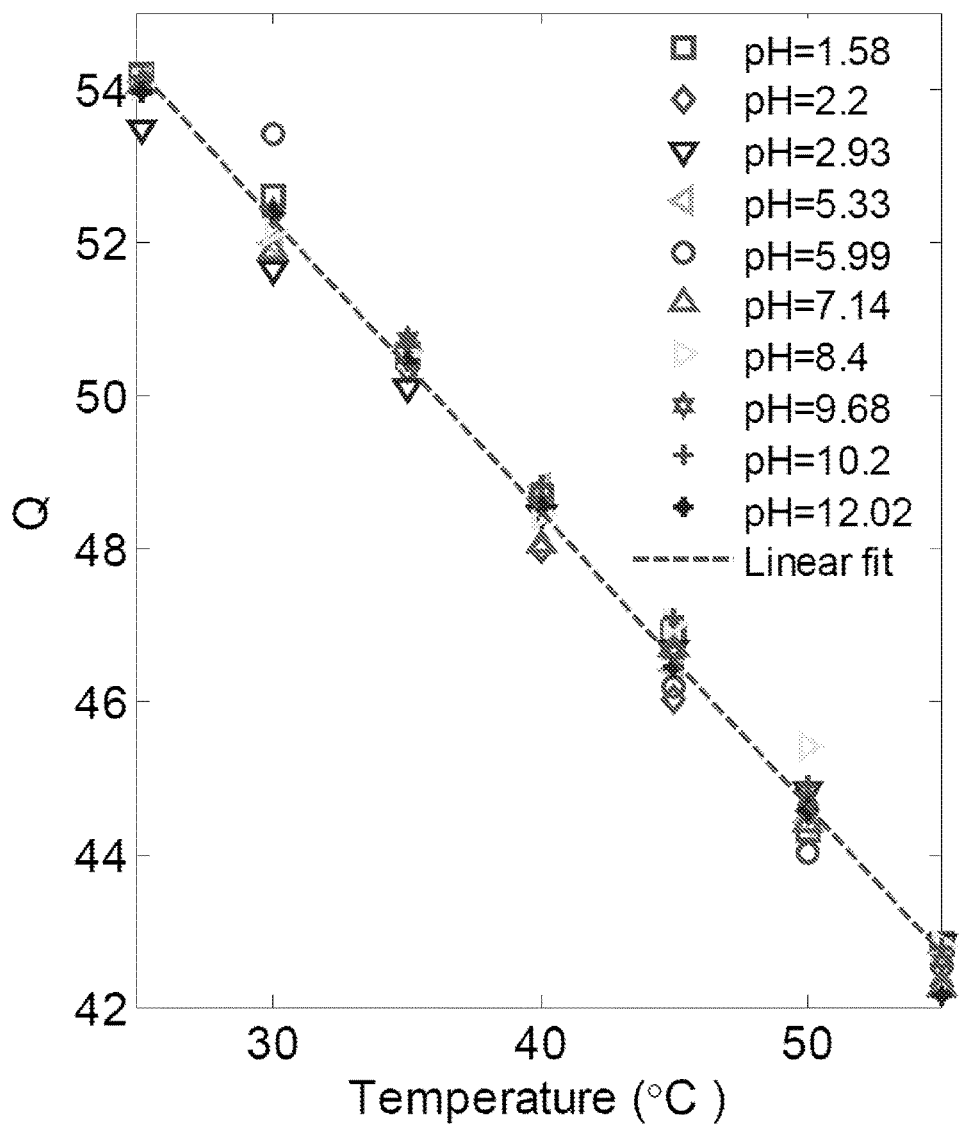
FIG. 14 is graph of the quality factor as a function of solution temperature for solutions having different pH values measured using the system of FIG. 6.

The experimental setup using the wireless passive sensor 400 is shown in FIG. 12. As shown, the coil 412 of the interrogator was located a distance 405 of 4 cm away from the coil of the passive sensor 400. Ten different pH solutions were measured with each solution's temperature varied from 25° C. to 55° C. The resonant frequency, f$_{0meas}$, and the quality factor, Q of the sensor were remotely monitored. FIG. 13 shows the frequency response of the sensor 400, Re{Z$_T$}, as measured by the impedance analyzer 442 for two different pH solutions at two different temperatures. FIG. 14 shows the measured quality factor, Q at different temperatures for different pH solutions 410. The temperature of the solution 410 can be extracted from the linear fit to data as $$T[°C.] = -2.61Q + 166.5. \quad (5)$$

Figure 15:
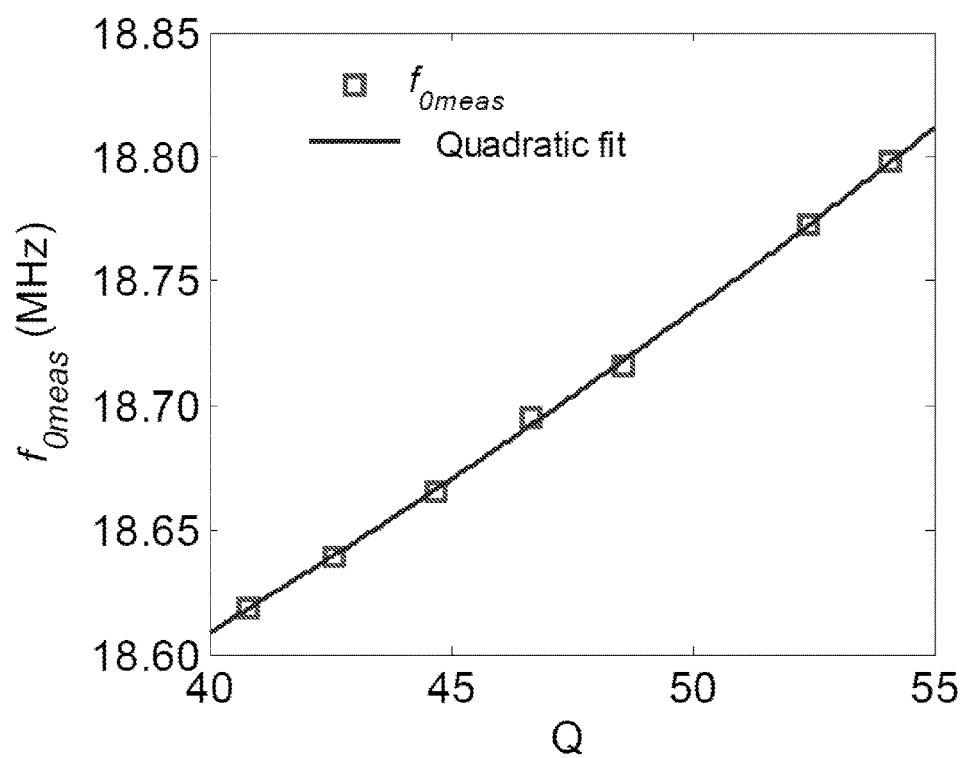
FIG. 15 is a graph of the resonant frequency of an exemplary sensor of the system of FIG. 6 versus quality factor for a solution (e.g., isothermal point) having a pH of 2.2.

According to Equation (2), the resonant frequency of the sensor 400 depends on $L_S$, C and Q. For our sensor 400, loss increases (Q goes down) as the temperature increases and thus the resonant frequency, $f_{0meas}$, decreases with Q. FIG. 15 shows the shift of $f_{0meas}$ due to Q for the isothermal point of a solution 410 having a pH of 2.2. As the electrode's 408 response, which in turns changes the junction capacitance, $C_j$, does not change with temperature for a solution 410 having a pH of 2.2, a quadratic fit (as shown in FIG. 15) was used to adjust the measured $f_{0meas}$ value to compensate for the change in Q. The quadratic fit providing the Q-adjusted resonant frequency may be given by $$f_{0Qadj}[MHz] = f_{0meas}[MHz] - 1.54 \times 10^{-4} Q^2 + 0.0011 Q + 0.4. \quad (6)$$

Figure 16:
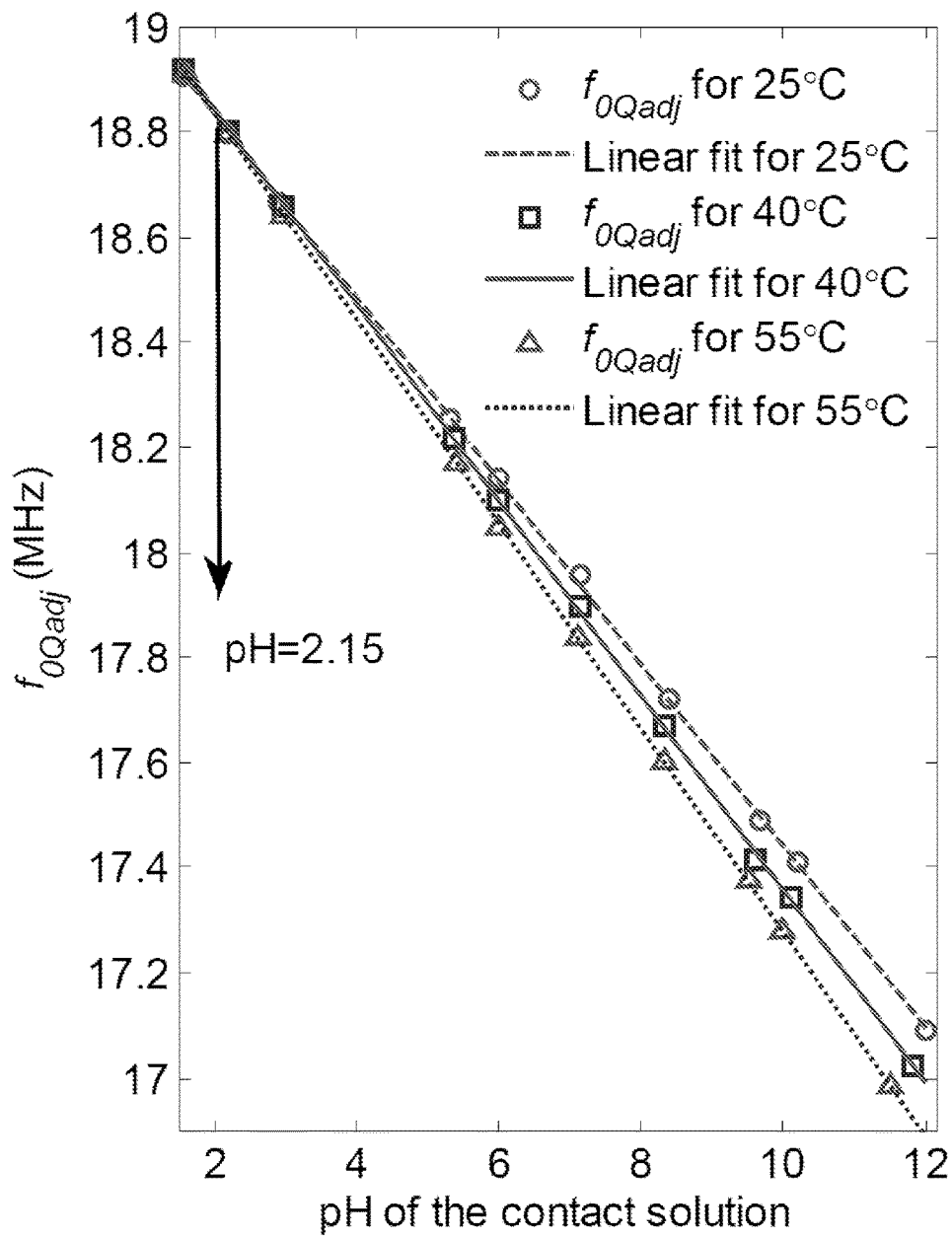
FIG. 16 is a graph of resonant frequency adjusted for Q change of an exemplary sensor of the system of FIG. 6 versus pH of the contact solution, as measured by commercial meter, for different solution temperatures.

FIG. 16 shows the Q-adjusted resonant frequency, $f_{0Qadj}$, for different pH solutions 410. It can be seen that, at a fixed temperature, $f_{0Qadj}$ has a linear response to pH. At 25° C., the linear fit over the 1.5-12 pH dynamic range indicates a slope of 174 kHz/pH and an intercept of 19.180 MHz. The slope of the linear fit increases with increase in temperature as 0.661 kHz/° C. (0.0038 pH/° C.) centered at 25° C. After compensating Q, the isothermal point is $pH_{Iso}$=2.15 ($f_{0Iso}$=18.806 MHz). The temperature compensated pH can then be found from the sensor 400 resonant frequency as $$pH = pH_{Iso} - \frac{1}{0.174}(1 - 0.0038(T[° C.] - 25))(f_{0Qadj}[MHz] - f_{0Iso}). \quad (7)$$

Figure 17:
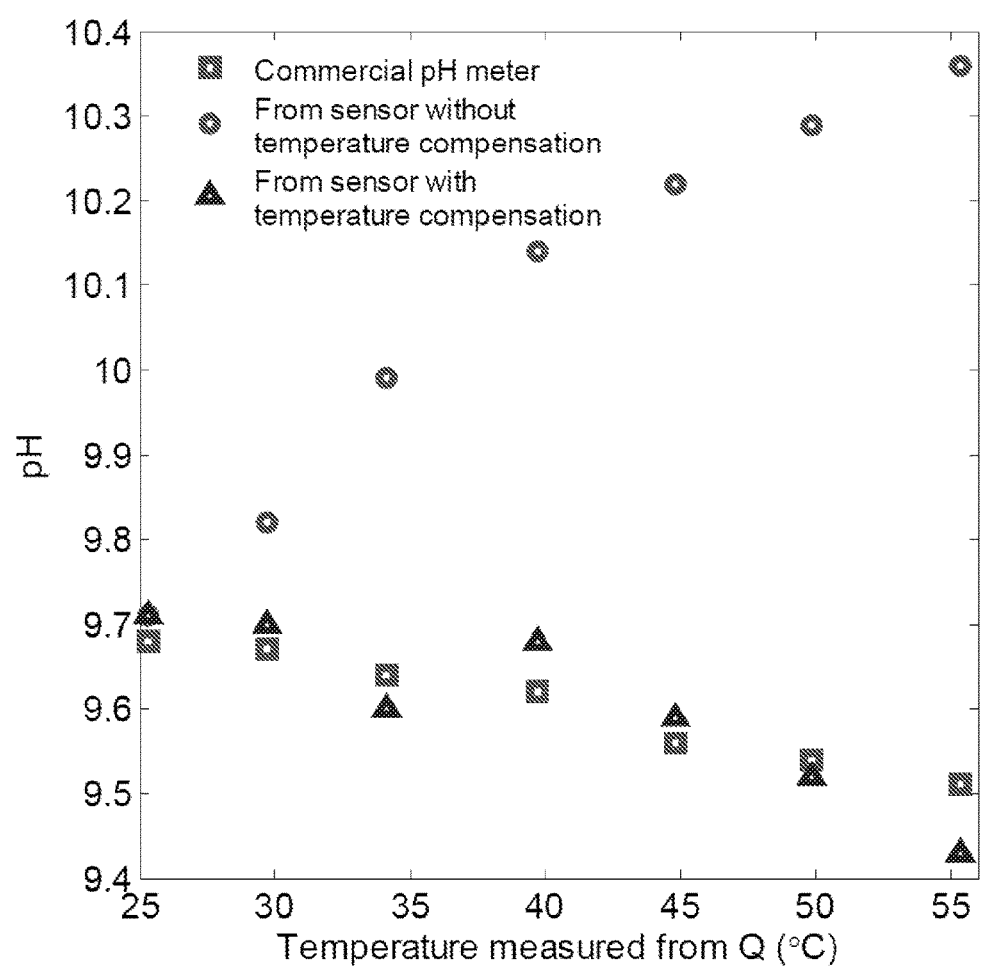
FIG. 17 is a graph of response of an exemplary pH sensor of the system of FIG. 6 employing temperature compensation and a commercial pH-meter as a function of the solution temperature.

FIG. 17 shows the measured pH of a solution 410 (e.g., prepared as having a pH of 9.68 at 25° C.) as a function of temperature. The solution 410 was measured with the wireless sensor 400 and a commercial temperature compensated pH meter. As shown, the sensor 400 can measure the pH of the solution with a plus or minus 0.1 pH accuracy when employing temperature compensation.

An integrated wireless passive sensor capable of simultaneous temperature and pH measurement has been described herein with respect to this example. The pH and temperature of different solutions could be wirelessly monitored by measuring the change of sensor's resonant frequency and quality factor, respectively. Results obtained from experimental data demonstrated that temperature from 25° C. to 55° C. and pH from 1.5 to 12 could be measured simultaneously. Further, monitoring temperature of the solution allowed temperature compensated pH measurement with 0.1 pH accuracy. Still further, the time-response of the sensor may be limited by the response time of the pH combination electrode and not by the sensor electronics or interrogator. For example, the time-response was less than 1 second for a 0.1 pH accuracy and 1.6 pH step change.

A Wireless Passive pH Sensor for Real-Time in-Fluid Milk Quality Monitoring

As bacteria grows during spoilage of milk, the pH of milk changes. Therefore, monitoring the pH of milk may provide a means for milk quality measurement. A wireless passive pH sensor for in-fluid milk quality monitoring is described herein with respect to this example. The sensor may be based on a passive LC coil resonator whose resonant frequency changes with the pH of the contact solution. An interrogator coil may be inductively coupled to the sensor coil and may be used to measure the sensor's resonant frequency by measuring the induced change in the impedance of the interrogator coil. In at least one embodiment, this exemplary sensor may be integrated with and/or embedded inside a milk package or carton, and may provide a solution to remote monitoring of milk freshness.

Figure 18:
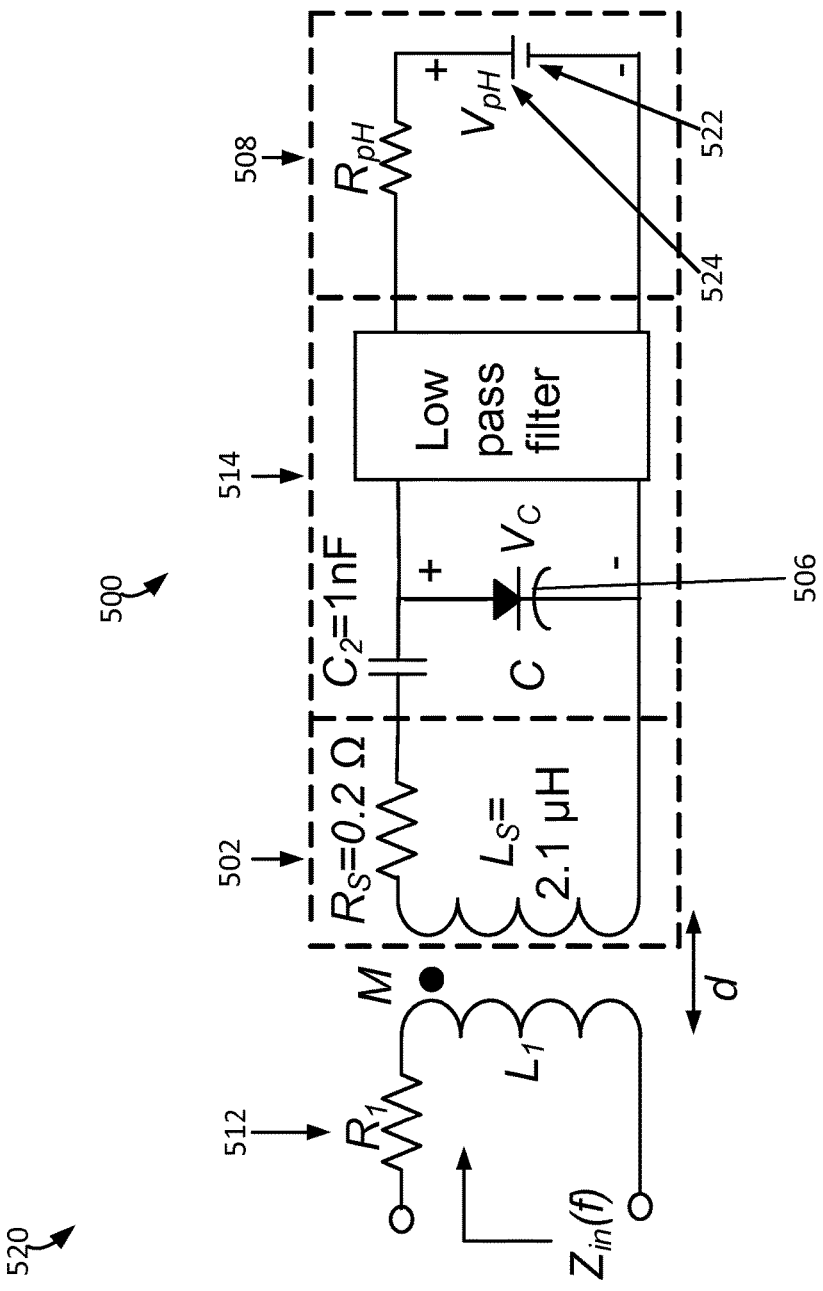
FIG. 18 is a circuit diagram of an exemplary system for use in the wireless passive transmission of pH of milk.

An equivalent circuit diagram 520 of the wireless passive pH sensor 500 is shown in FIG. 18, and includes the interrogation circuit/coil 512 inductively couplable to the sensor 500. In the remote sensor 500, a spiral inductor 502 is connected in parallel with a voltage dependent capacitor 506 (e.g., varactor) based voltage sensing circuit 514. A pH combination electrode 508 is connected in parallel with the varactor 506 and provides a biasing voltage to the varactor 506. Although the sensor 500 does not include a temperature compensation component such as, e.g., temperature dependent resistor 404 as described herein with reference to FIG. 7, the sensor 500 may include a temperature compensation component in additional embodiments.

The pH combination electrode 508 in the exemplary sensor 500 may include an iridium/iridium oxide sensing electrode 522 and a silver/silver chloride reference electrode 524. An iridium/iridium oxide electrode 522 may have the advantages of easy preparation, small size, continuous detection ability as well as a fast and stable response in aqueous, non-aqueous, non-conductive, and even corrosive media, and further may provide a linear response to pH with reference to a silver/silver chloride electrode 524 from a pH of 2 to a pH of 12 with a low impedance. No requirement for pretreatment may exist for the electrode 508, and further the electrode 508 may have negligible interference of ions and complexing agents. Such pH combination electrodes maybe used in technical media, such as fuels, food applications and in biological media.

In the circuit 520 shown in FIG. 18, $L_S$ and $R_S$ are the series inductance and resistance of the sensor coil 502, respectively, and $L_1$ and $R_1$ are the series inductance and resistance of the interrogator coil 512, respectively. M is the interrogator-sensor coil coupling factor. C is the small signal junction capacitance of the voltage dependent capacitor 506 (e.g., varactor diode) in the sensing circuit 514. In the reverse bias state, C may be approximated by $C(V_C)=C_0(1-V_C/\phi)^{-1/2}$, where $C_0$ is the junction capacitance at zero bias, $\phi$ is the junction built in potential, and $V_C$ is the bias voltage applied across the varactor 506. $V_{pH}$ and $R_{pH}$ are the potential difference and the cell resistance, respectively, developed at the pH combination electrode 508 when in contact with a solution. In the circuit, $R_3$ and $C_2$ may act as a low pass filter so that the resonator is sensitive to low frequency variations in $V_{pH}$. For a small interrogator source oscillation amplitude, small M, and $R_{pH} \ll (R_2+R_3)$, the approximation $V_C \cong V_{pH}$ can be applied. As $C_1 \gg C(V_C)$, the resonant frequency, $f_0$, of the sensor 500 can be approximated by:

$$f_0 \cong \frac{1}{2\pi\sqrt{L_S C(V_{pH})}}. \quad (8)$$

Therefore, the of the contact solution, which is indicated by $V_{pH}$, can be monitored by tracking the $f_0$ of the sensor 500.

Referring to FIG. 18, near the resonant frequency, $f_0$, the impedance, $Z_{in}$, seen by the interrogator may given by $$Z_{in}(f) = Z_1 + Z_T = R_1 + j2\pi f L_1 + \frac{(2\pi f)^2 M^2}{Z_S}, \quad (9)$$

where is the interrogator source frequency and $Z_S \cong R_S + j2\pi fL_S + (R_T/(1+j2\pi fCR_T))$ is the sensor series impedance. In the exemplary system, the resonant frequency was obtained from the maximum of the real part of the impedance using a quadratic curve-fitting algorithm (see, e.g., M. P. Robinson and J. Clegg, "improved determination of Q-factor and resonant frequency by a quadratic curve fitting method," *IEEE Transaction on Electromagnetic Compatibility*, vol. 47, no. 2, pp. 399-402, May 2005). The impedance, $Z_{in}$, in Equation (9) may include two components: $Z_1 = R_1 + j2\pi fL_1$, due to the self-impedance of the interrogator coil; and $Z_T = (2\pi f)^2 M^2 / Z_S$, due to the sensor coupling. To remove the self-impedance of the interrogator coil 512, a background subtraction, using the measured impedance of the interrogator coil 512 when the sensor 500 was absent, was implemented prior to measuring the sensor response.

The iridium/iridium oxide (Ir/IrO$_x$) sensing electrode 522 was prepared by a direct oxidation method. For example, an Ir metal wire (e.g., 0.5 mm in diameter, 99.8% purity, obtained from Alfa AESAR) of about 10 mm in length was ultrasonically cleaned with 6M HCl solution followed with de-ionized water. Then, the clean wire was then oxidized by bringing it to a temperature of 800° C. in an electric oven for 45 minutes after wetting its surface with 1M NaOH solution. The wetting and heating process was repeated six times until a blue-black coating was formed on the surface. The electrode 522 was immersed in boiling DI water for an hour, and then in DI water at room temperature for 30 days to reduce aging effects. A small area (e.g., about 2 mm in length) of iridium oxide film at one end was removed (e.g., scraped off) and connected to an insulated wire using silver epoxy. Silicone sealant (e.g., GE Silicone I) was applied over the connection area for electric insulation.

The silver/silver chloride (Ag/AgCl) reference electrode 524 (e.g., obtained from DOCXS biomedical products and accessories) was 0.5 ram in diameter and 8 mm in length. Soft silver wire was attached to the electrode 524 for electrical connection, an insulated wire was connected to the silver wire, and the connection area was electrically insulated with silicone sealant.

Figure 19:
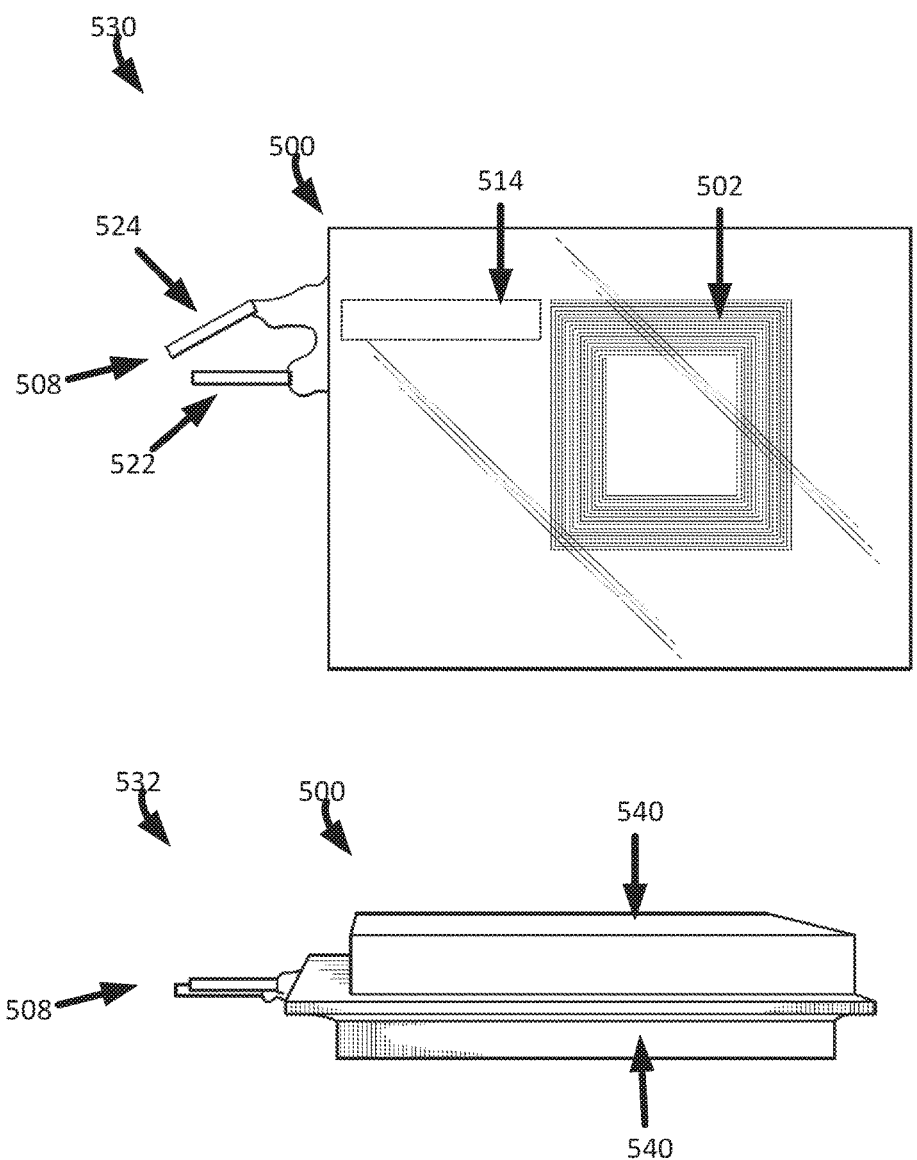
FIG. 19 is a photograph of an exemplary sensor for use in the system of FIG. 18.

An exemplary sensor 500, as shown in the top plan view 530 and the side view 532 depicted in FIG. 19, was constructed using the Ir/IrO$_x$ electrode 522 and Ag/AgCl electrode 524. The sensor 500 was designed to have a resonant frequency, $f_0$, near 18 MHz. The sensor inductor 502 and the voltage sensing circuit 514 were fabricated on a 4 cm×3 cm single sided FR4 printed circuit board (PCB) with surface mount capacitors and resistors. The inner and outer dimensions of the square, eight-turn planar spiral inductor were 1.45 cm and 2.68 cm, respectively, producing $L_S = 2.1$ μH and $R_S = 2.2\Omega$ at 18 MHz. The junction capacitance of the varactor (e.g., NXP BB202) used in the voltage sensing circuit 514, C, varied in the range of 35.04 pF-22.95 pF for reverse bias voltages between 0 V and 1 V, respectively. For in-fluid monitoring, the sensor 500 was sandwiched between dielectric spacers 540 to encapsulate, and reduce parasitic capacitive coupling and eddy current loss. For this, 6 mm thick plexiglass was used as the dielectric spacer 540.

The electrode resistance, $R_{pH}$, for pH solutions in the range of 1.5-12 was approximately 3.16 MΩ. The Ag/AgCl and Ir/IrO$_x$ electrodes 524, 422 were connected to the positive and negative terminals of the voltage sensing circuit 514, respectively.

The interrogator coil (not shown) was 5.1 cm in diameter and constructed of 5 turns of insulated copper wire of 1.2 mm diameter, producing $L_1 = 2.35$ μH, $R_1 = 334.13$ mΩ and a self-resonant frequency, $f_{res} = 28.32$ MHz. The resonant frequency of the sensor 500 was determined by measuring the real part of the impedance of the interrogator coil, Re{$Z_{in}$}, when inductively coupled to the sensor coil 502. The interrogator coil impedance was measured using an impedance analyzer (e.g., Agilent 4294A) with the voltage source level of the analyzer set to 25 mV.

Figure 20:
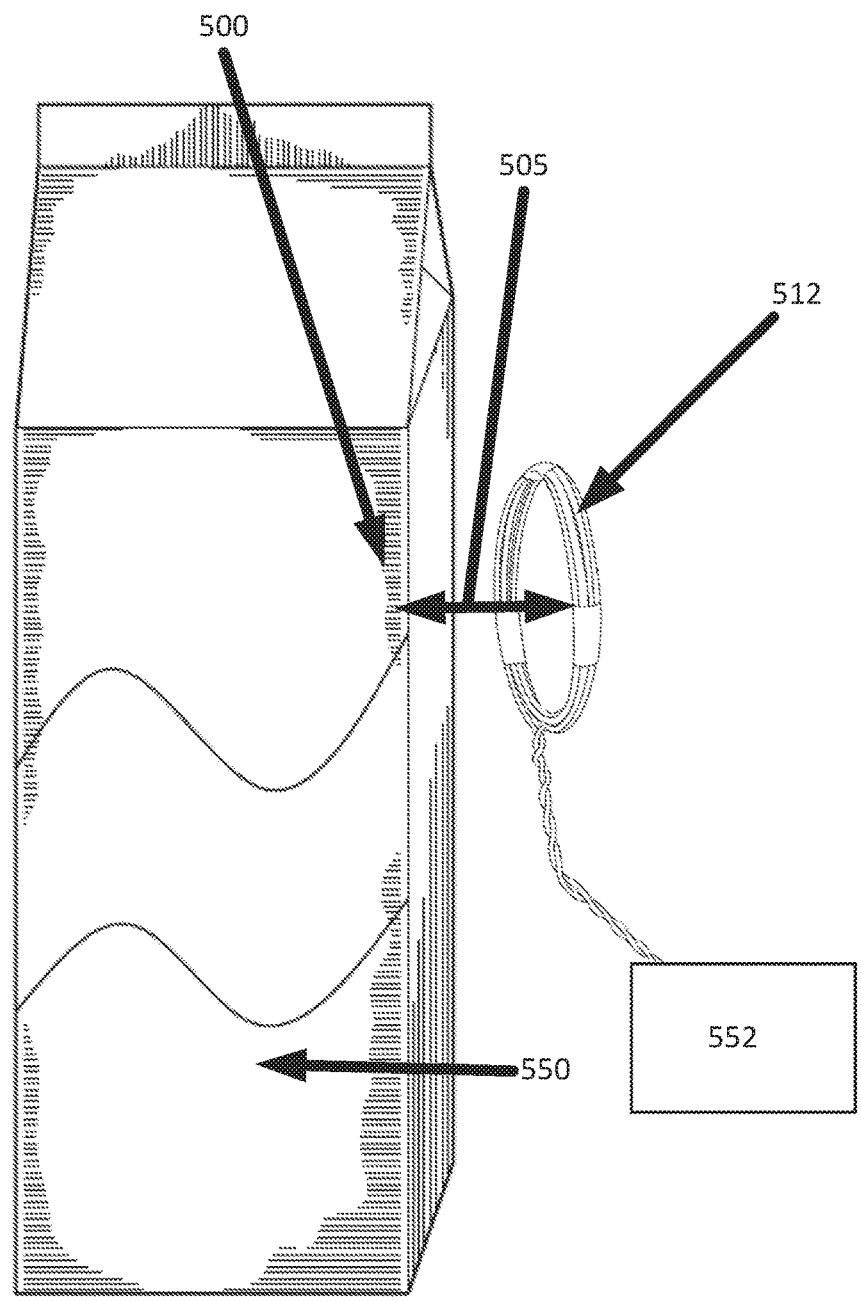
FIG. 20 is a photograph of the system of FIG. 18.
Figure 21:
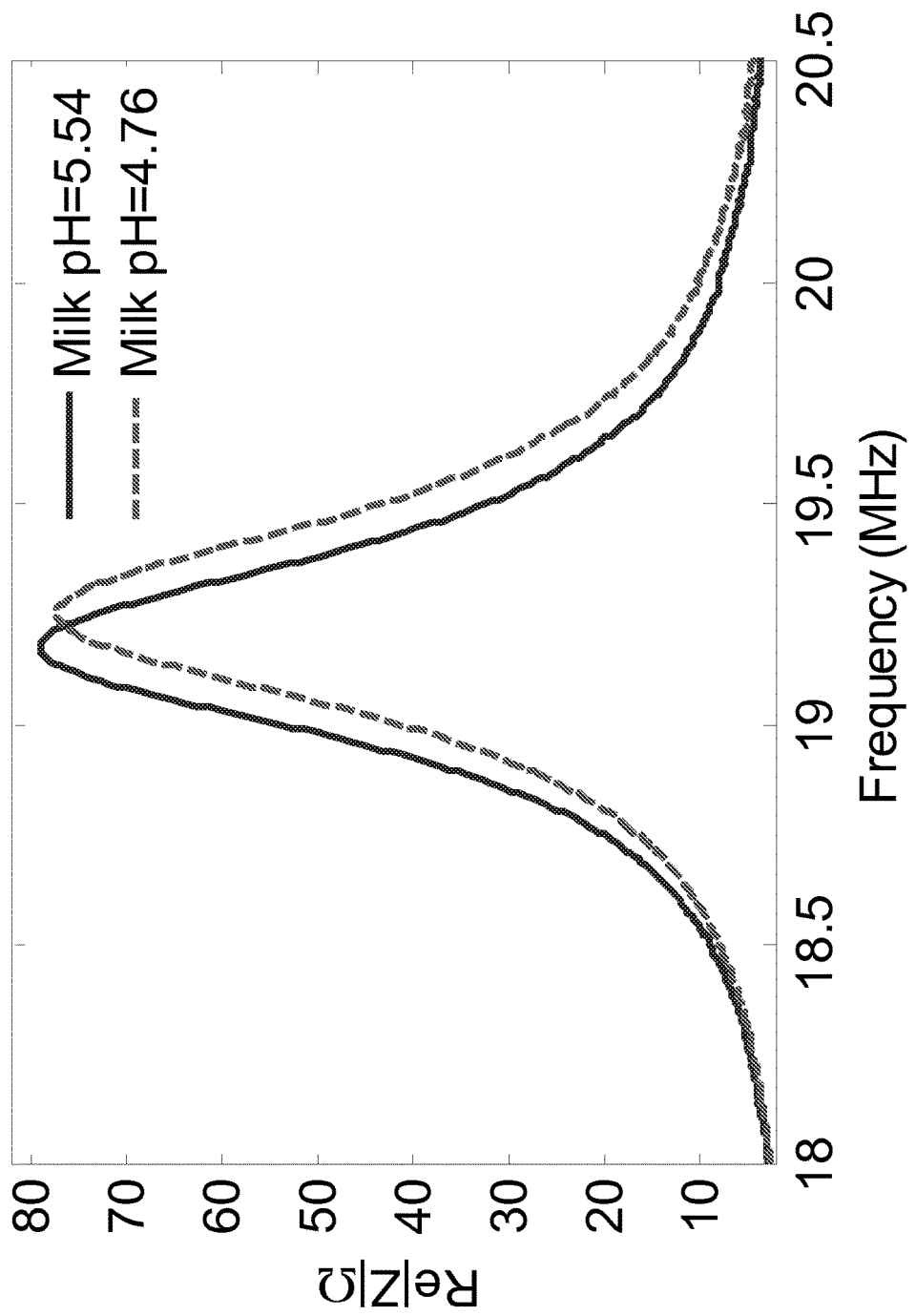
FIG. 21 is a graph of an impedance frequency response measured using the system of FIG. 18 for different milk pH values.

As shown in FIG. 20, the sensor 500 was embedded in a standard container 550 containing 2% milk with a very small amount of yogurt (e.g., used for rapid bacteria growth). The container 550 was stored at 25° C. for 3 days. The resonant frequency, $f_0$, of the sensor 500 was monitored at a distance 505 of 5 cm using an interrogator coil 512 and an impedance analyzer 552. The pH of the milk was also measured using a commercial pH-meter. FIG. 21 shows the impedance frequency response of the sensor 500 for two different milk pH values.

Figure 22:
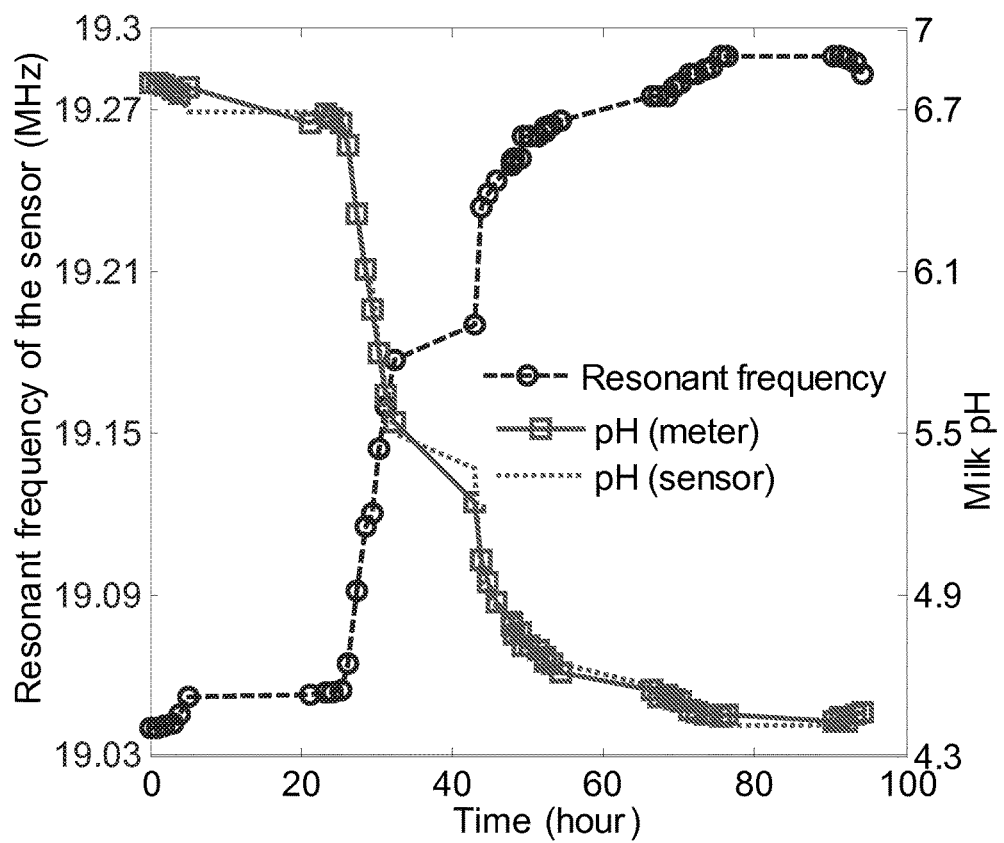
FIG. 22 is a graph of resonant frequency of and the pH measured by an exemplary sensor of the system of FIG. 18 and the pH of milk measured with a pH-meter using the linear calibration curve over time.

Variation of the resonant frequency of the sensor 500 and milk pH (e.g., measured using the sensor 500 and commercial pH-meter) over the 3 days is shown in FIG. 22, which may indicate the ability of the sensor 500 to track pH with a maximum deviation of 0.12 pH from the commercial pH-meter value.

Figure 23:
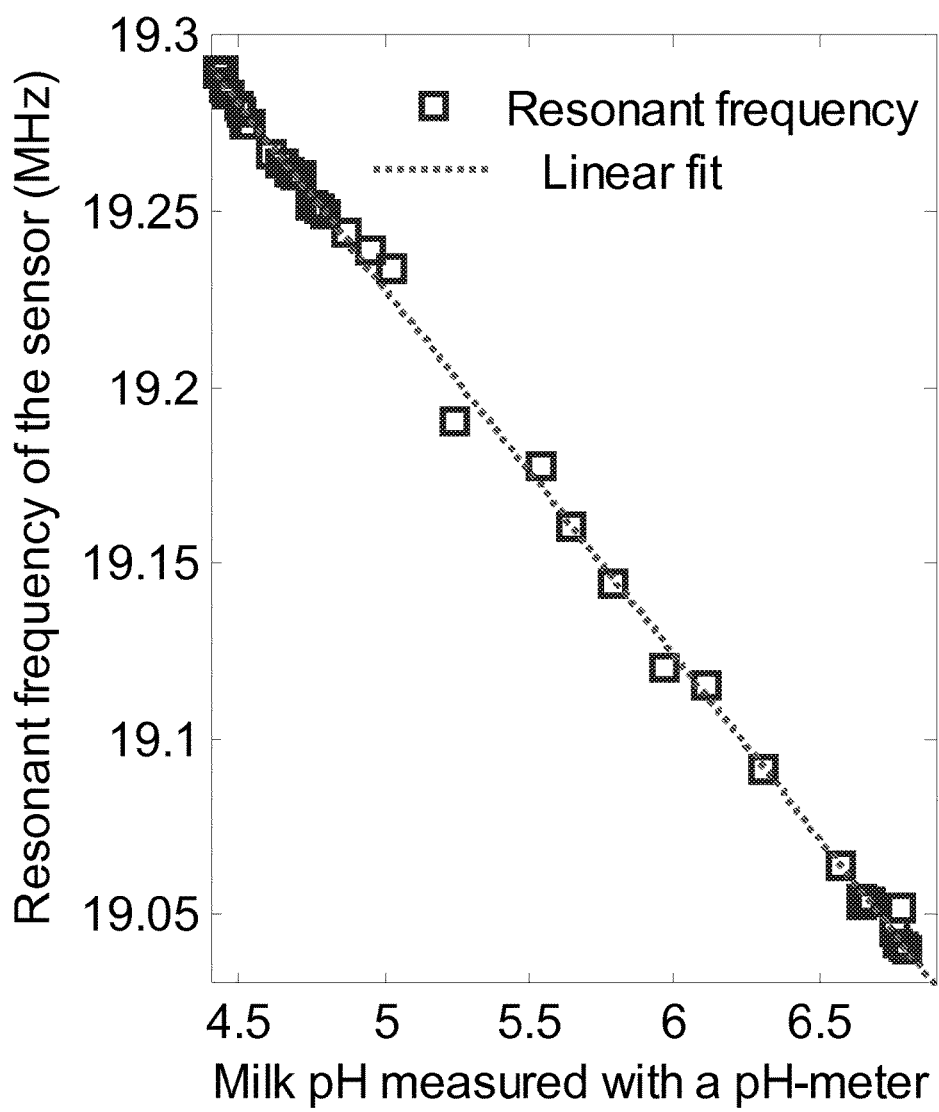
FIG. 23 is a graph of a resonant frequency of an exemplary sensor of the system of FIG. 18 versus the pH of milk.

FIG. 23 shows the relationship between the pH of milk (e.g., measured with the commercial pH-meter) and the resonant frequency of the sensor 500. A linear fit may be given by $f_0$ (MHz)=−0.10 pH+19.751 from a pH of 6.8 to a pH of 4.4 pH and may indicate a 100 kHz/pH sensitivity with a maximum deviation of 11.7 kHz (<0.12 pH) from linear fit. Further, the response time of the sensor may be limited by the response time of the pH combination electrode 508 and was measured to be less than 20 seconds for a step change of 1.6 pH.

A wireless passive pH sensor capable of real time in-fluid milk quality monitoring has been described here with respect to this example. As described, during milk spoilage, pH could be wirelessly monitored by measuring the change of a sensor's resonant frequency. Results obtained from the experiment have demonstrated that the pH of milk from a pH of 6.8 to a pH of 4.4 could be measured within 0.12 pH accuracy.

Wireless Passive Sensor for pH Monitoring Inside a Small Bioreactor

An exemplary wireless passive pH sensor 600 that can be integrated with (e.g., embedded or located inside) a bioreactor is described herein with respect to FIGS. 24-28. The sensor 600 may be robust and sterilizable. Further, the sensor 600 may be based on a passive LC resonator whose resonant frequency changes with the pH of a medium. An interrogator inductor may be inductively coupled to the sensor 600 to measure change in the resonant frequency of the sensor 600 by measuring the induced change in the impedance of the interrogator. Although the sensor 600 does not include a temperature compensation component such as, e.g., temperature dependent resistor 404 as described herein with reference to FIG. 7, the sensor 600 may include a temperature compensation component in additional embodiments.

Figure 24:
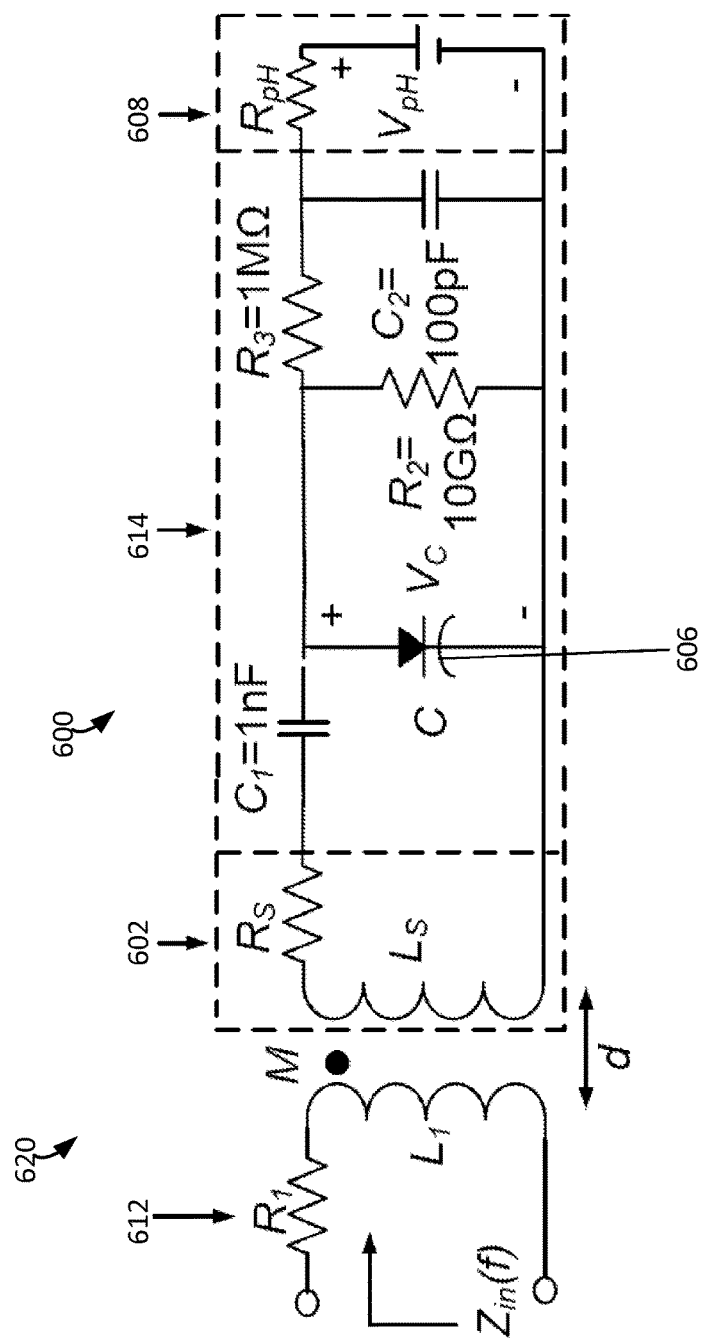
FIG. 24 is a circuit diagram of an exemplary system for use in the wireless passive transmission of pH of a material inside of a bioreactor.

An equivalent circuit diagram 620 of the exemplary wireless passive pH sensor 600 is depicted in FIG. 24. The circuit diagram 620 includes an interrogation circuit/coil 612 inductively coupled to the sensor 600. In the sensor 600, a spiral inductor 602 is connected in parallel with a voltage dependent capacitor 606 (e.g., varactor) of a voltage sensing circuit 614. A pH combination electrode 608 is connected in parallel with the varactor 606 and may provide a biasing voltage to the varactor 606. The pH combination electrode 608 in the exemplary sensor 600 may include an iridium/iridium oxide sensing electrode and a silver/silver chloride reference electrode.

In the circuit diagram 620 shown in FIG. 24, $L_S$ and $R_S$ are the series inductance and resistance of the sensor coil 602, respectively, and $L_1$ and $R_1$ are the series inductance and resistance of the interrogator coil 612, respectively. M is the interrogator-sensor coil coupling factor. C is the small signal junction capacitance of the voltage dependent capacitor 606 (e.g., varactor diode) in the sensing circuit 614. In the reverse bias state, C may be approximated by $C(V_C) = C_0(1-V_C/\phi)^{-1/2}$, where $C_0$ is the junction capacitance at zero bias, $\phi$ is the junction built in potential and $V_C$ is the bias voltage applied across the varactor. $V_{pH}$ and $R_{pH}$ are the potential difference and the cell resistance, respectively, developed at the pH combination electrode 608 when in contact with a solution. In the circuit 614, a low pass filter was included so that the resonator is sensitive to low frequency variations in $V_{pH}$. For a small interrogator source oscillation amplitude, small M, and $R_{pH} \ll (R_2 + R_3)$, the approximation $V_C \cong V_{pH}$ can be applied. As $C_1 \gg C(V_C)$, the resonant frequency, $f_0$, of the sensor can be approximated by $$f_0 \cong \frac{1}{2\pi\sqrt{L_S C(V_{pH})}} \tag{10}$$

Therefore, pH of the contact solution, which is indicated $V_{pH}$, can be monitored by tracking the $f_0$ of the sensor 600.

Referring to FIG. 24, near the resonant frequency, $f_0$, the impedance, $Z_{in}$, seen by the interrogator inductor 612 may be given by $$Z_{in}(f) = Z_1 + Z_T = R_1 + j2\pi f L_1 + \frac{(2\pi f)^2 M^2}{Z_S} \tag{11}$$

where f is the interrogator source frequency and $Z \approx R_S + j2\pi f L_S + (1/(j2\pi f C))$ is the sensor series impedance. In the exemplary system, the resonant frequency was obtained from the maximum of the real part of the impedance using a quadratic curve-fitting algorithm. The impedance, $Z_{in}$, in Equation (11) may include two components: $Z_1 = R_1 + j2\pi f L_1$, due to the self-impedance of the interrogator inductor 612; and $Z_T = (2\pi f)^2 M^2/Z_S$, due to the sensor coupling. To remove the self-impedance of the interrogator coil 612, a background subtraction, using the measured impedance of the interrogator coil when the sensor was absent, was implemented prior to measuring the sensor response.

The iridium/iridium oxide (Ir/IrO$_x$) sensing electrode of the combination electrode 608 was prepared by a direct oxidation method. Ir metal wire (e.g., 0.5 mm in diameter, 99.8% purity, obtained from Alfa AESAR) of about 10 mm in length was ultrasonically cleaned with 6M HCl solution followed with de-ionized water. Then, the clean wire was oxidized by bringing the wire to a temperature of 800° C. in an electric oven for 45 minutes after wetting its surface with 1M NaOH solution. The wetting and heating process was repeated six times until a blue-black coating was formed on the surface. The electrode was then immersed in boiling DI water for an hour, and then in DI water at room temperature for 30 days to reduce aging effects. A small area (e.g., about 2 mm in length) of iridium oxide film at one end was removed (e.g., scraped off) and connected to an insulated wire using silver epoxy. High temperature epoxy was applied over the connection area for electric insulation.

The silver/silver chloride (Ag/AgCl) reference electrode of the combination electrode 608 was prepared from silver wire by an electroplating method. 10 mm of Ag wire (e.g., 1 mm in diameter, 99.8% purity, obtained from Alfa AESAR) was polished using sandpaper, and an insulated wire was connected to a small area of the polished Ag wire (e.g., about 2 mm in length) using silver epoxy. High temperature epoxy was applied over the connection area for electric insulation, and a layer of AgCl was formed on the remaining 8 mm of the polished Ag wire by applying +0.5 V for 50 seconds in a 0.1 M potassium chloride (KCl) solution. An immobilized electrolyte was freshly prepared by saturating 12 ml, of tetrahydrofuran (THF) with KCl at room temperature and then adding 0.4 g of Polyvinyl chloride (PVC). The Ag/AgCl wire was dip-coated in the immobilized electrolyte solution and dried in a house vacuum-evacuated desiccator for 48 hours. After drying, the electrode was dip-coated with a protective nafion layer (or, e.g., a polyurethane layer) to prevent the leakage of chloride ions. Following the dip-coating, the electrode was cured in a pump-evacuated oven for 1 hour at 120° C., stored in a desiccator for seven days, placed in DI water for 24 hours, and then stored in a desiccator until it was used (see, e.g., M. A. Nolan, S. H. Tan and S. P. Kounaves, "Fabrication and characterization of a solid state reference electrode for electroanalysis of natural waters with ultramicroelectrodes," Anal. Chem., vol. 69, pp. 1244-1247, March 1997).

Figure 25:
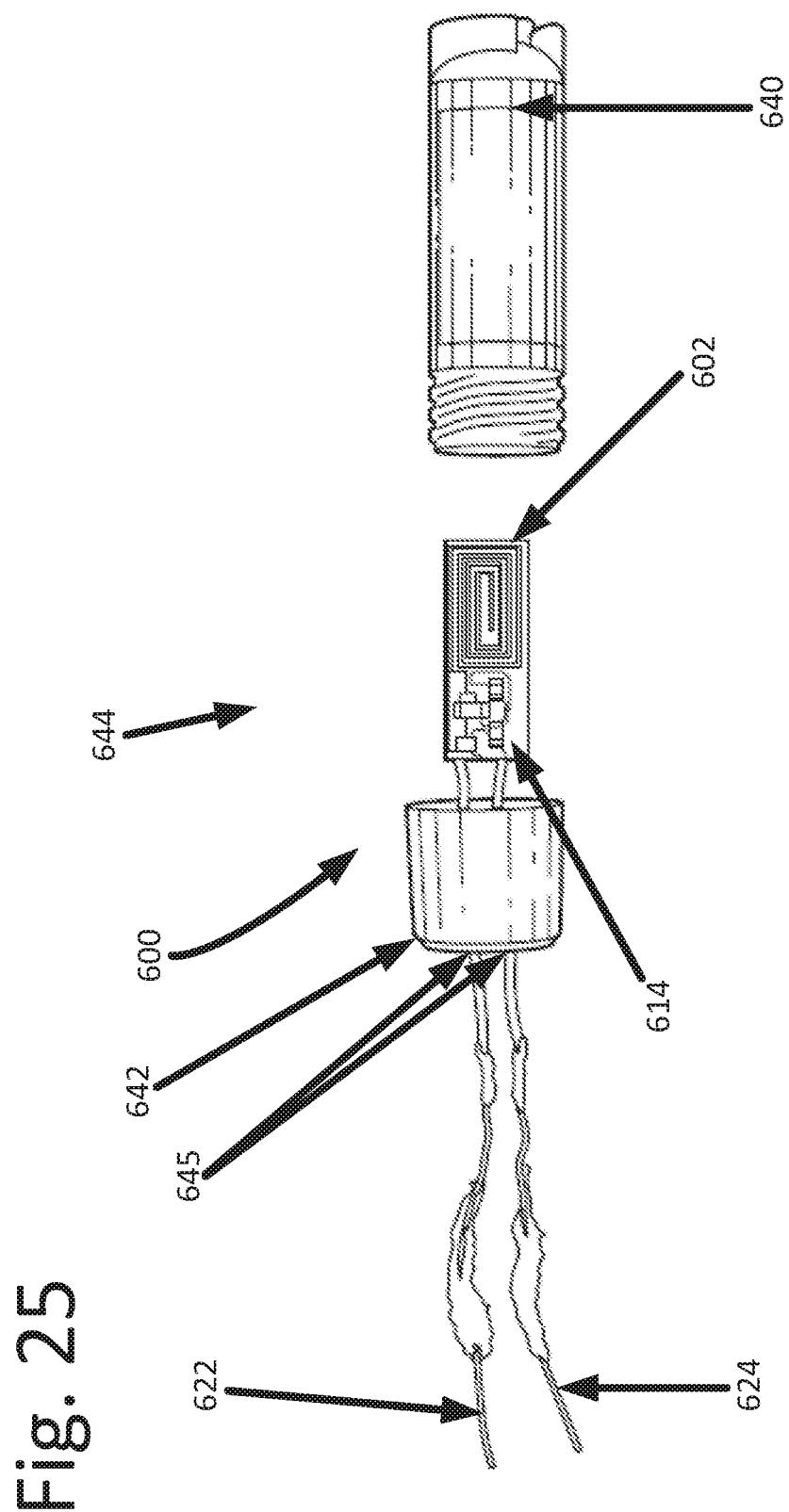
FIG. 25 is a photograph of an exemplary sensor for use in the system of FIG. 24.

The sensor 600, as shown in FIG. 25, was constructed using the Ir/IrO$_x$ electrode 622 and Ag/AgCl electrode 624 as described herein. The sensor 600 was designed to have a resonant frequency, $f_0$, near 77 MHz. The sensor inductor 602 and the voltage sensing circuit 614 were fabricated on a 20 mm×6 cm single sided FR4 printed circuit board (PCB) with surface mount capacitors and resistors. The inner and outer dimensions of the rectangular, four-turn planar spiral inductor were 6.5 mm×1.2 mm and 12 mm×5.5 mm, respectively, producing $L_S$=0.13 µH and $R_S$=1.25Ω at 77 MHz. The junction capacitance of the varactor 606 (e.g., NXP BB202) used in the voltage sensing circuit 614, C, varied from 35.04 pF to 22.95 pF for reverse bias voltages from 0 V to 1 V, respectively. For in-fluid monitoring, the sensor 600 was hermetically sealed in a polypropylene vial to encapsulate, and reduce parasitic capacitive coupling and eddy current loss. The vial includes a cup portion 640 and a cap portion 642 couplable to the cup portion 640 to define a hermitically-sealed cavity therein.

Locations 645 where the electrodes extended from (e.g., came out of) the vial cap 642 were sealed properly with high temperature epoxy. The electrode resistance, $R_{pH}$, for pH solutions in from a pH of 1.5 to a pH of 12 was approximately 3.16 MΩ. The Ag/AgCl and Ir/IrO$_x$ electrodes 624, 622 were connected to the positive and negative terminals of the voltage sensing circuit 614, respectively.

The interrogator (not shown) was fabricated on a 32 mm×32 mm single sided FR4 printed circuit board. The inner and outer dimensions of the square, eight-turn planar spiral inductor 612 were 3 mm×3 mm and 13 mm×13 mm, respectively, producing $L_S$=0.82 µH, $R_S$=2.2Ω at 77 MHz and a self-resonant frequency, $f_{res}$=97.3 MHz. The resonant frequency of the sensor 600 was determined by measuring the real part of the impedance of the interrogator coil 612, Re{$Z_{in}$}, when inductively coupled to the sensor coil 602. The interrogator coil impedance was measured using an impedance analyzer (e.g., an Agent 4294A) with the voltage source level of the analyzer set to 25 mV.

Similar to FIG. 5, the sensor 600 was embedded in a standard shake flask (e.g., a bioreactor) containing a medium and a carbon source. The medium was prepared from 10 grams (g)/liter (L) yeast extract and 20 g/L peptone. Glycerol (e.g., 13 mL of 50% glycerol solution to give a final concentration of 440 millimolar (M) was used as the carbon source. The total volume of the medium and carbon source was 200 milliliter (mL). The shake flask and the sensor 600 were both sterilized. A commercial pH probe and oxygen tubing were sterilized and inserted into the bioreactor to track the pH of the medium and supply oxygen, respectively. 40 mL of Yarrowia lipolytica cells were harvested during mid-exponential growth stage. The bioreactor was centrifuged to separate the cells from the supernatant, and the liquid volume was reduced to 10 mL, concentrating the biomass in the inoculum by a factor of 4.2 mL of Yarrowia lipolytica cells were inoculated to the bioreactor filled earlier medium and carbon source for fermentation.

Figure 26:
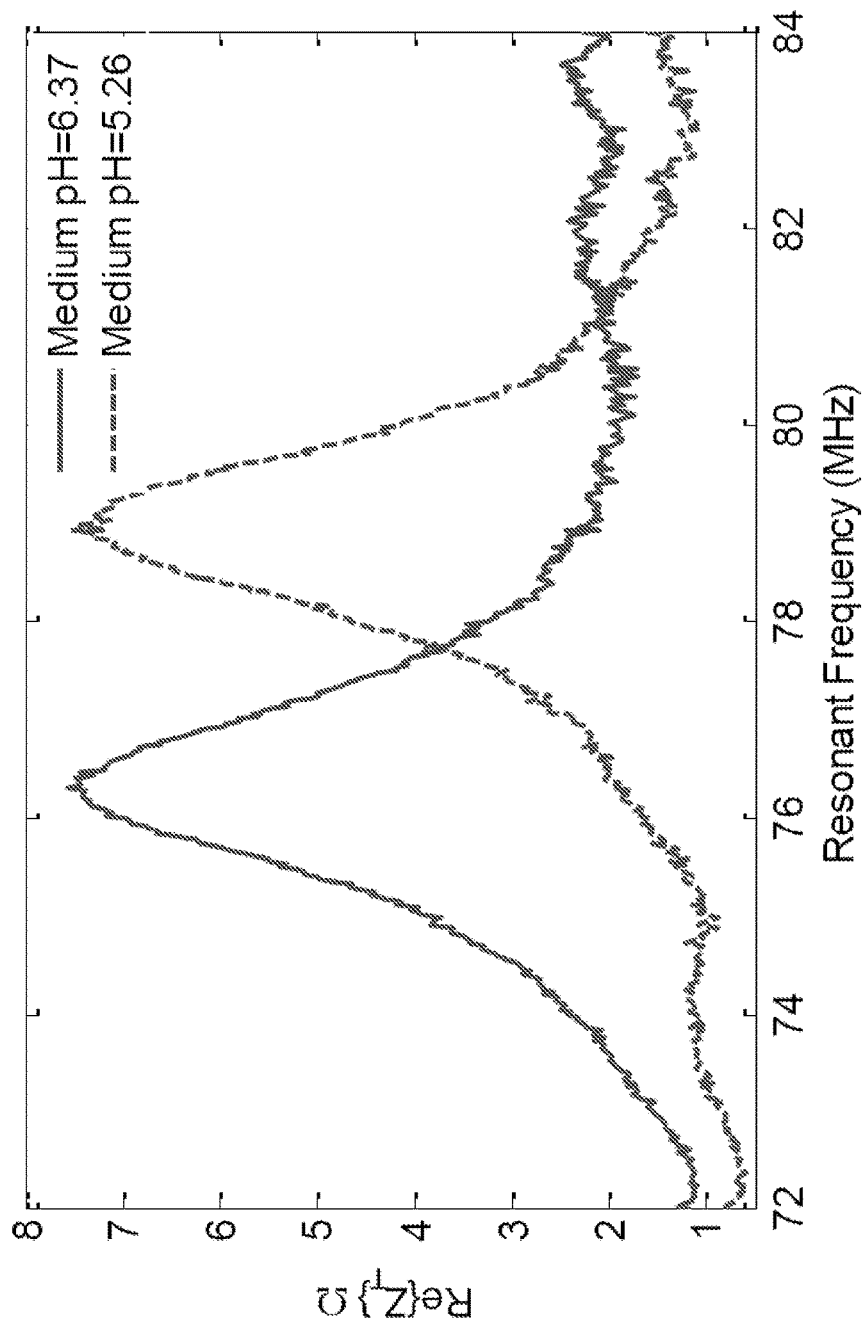
FIG. 26 is a graph of an impedance frequency response for two mediums, each having a different pH value, using the system of FIG. 24.

The medium was stirred at a constant speed of 100 rpm at 30° C. The resonant frequency, $f_0$, of the sensor 600 was monitored at half an hour intervals at a distance of 2 cm using the interrogator inductor 612 and an impedance analyzer. A data logger (e.g., connected to the pH probe) stored the measured pH of medium. FIG. 26 shows the impedance frequency response of the sensor 600 for two mediums, each having different pH values.

Figure 28:
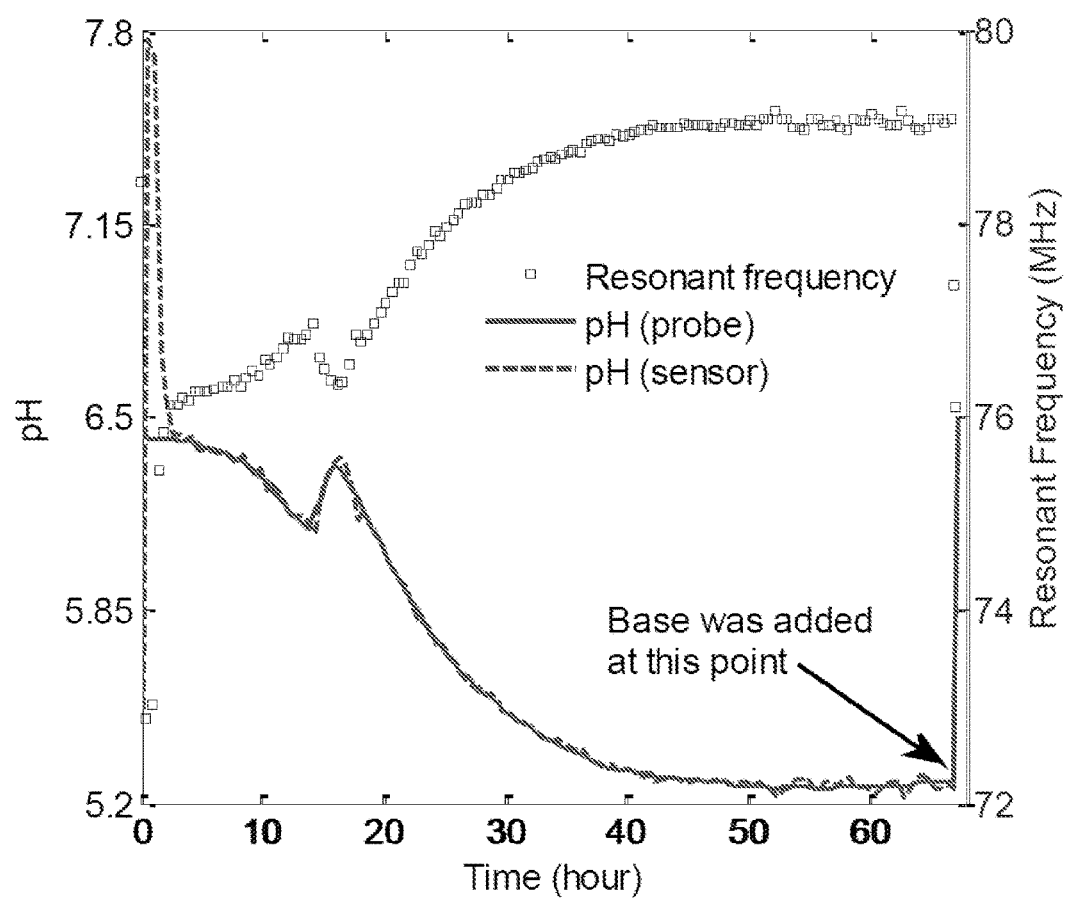
FIG. 28 is a graph of resonant frequency of and the pH measured by an exemplary sensor of the system of FIG. 24 and the of the medium as measured with a commercial pH probe using the linear calibration curve in FIG. 27 over a period of 67 hours.

Variation of the resonant frequency of the sensor 600 and the pH of the medium (e.g., measured using the sensor 600 and commercial pH-probe) over 67 hours is shown in FIG. 28. As shown, after a period of 2.5 hours, the pH monitored by the sensor 600 was in good agreement with the pH measured by the commercial pH probe over the course of the fermentation period with a maximum deviation of 0.07 pH. The initial difference in the wireless sensor result may be due to stabilization of the reference electrode. For example, the reference electrode was stored in desiccator and required 2.5 hours in the medium before its potential stabilized (see, e.g., J. B. Ong, Z. You, J. Mills-Beale, E. L. Tan, B. D. Pereles and K. G. Ong, "A wireless, passive embedded sensor for real time monitoring of water content in civil engineering materials," *IEEE Sensors J.*, vol. 8, issue 12, pp. 2053-2058, December 2008). To test the repeatability of the sensor 600, base was added to the medium after 67 hours (e.g., when fermentation was completed) and the pH of the medium increased to 6.5 from 5.26 in two steps. In sum, the data depicted in FIG. 28 shows that the sensor 600 produced repeatable results after the 67 hour test, and further, also indicates that sensor 600 was not affected or damaged inside the bioreactor and/or by the medium.

Figure 27:
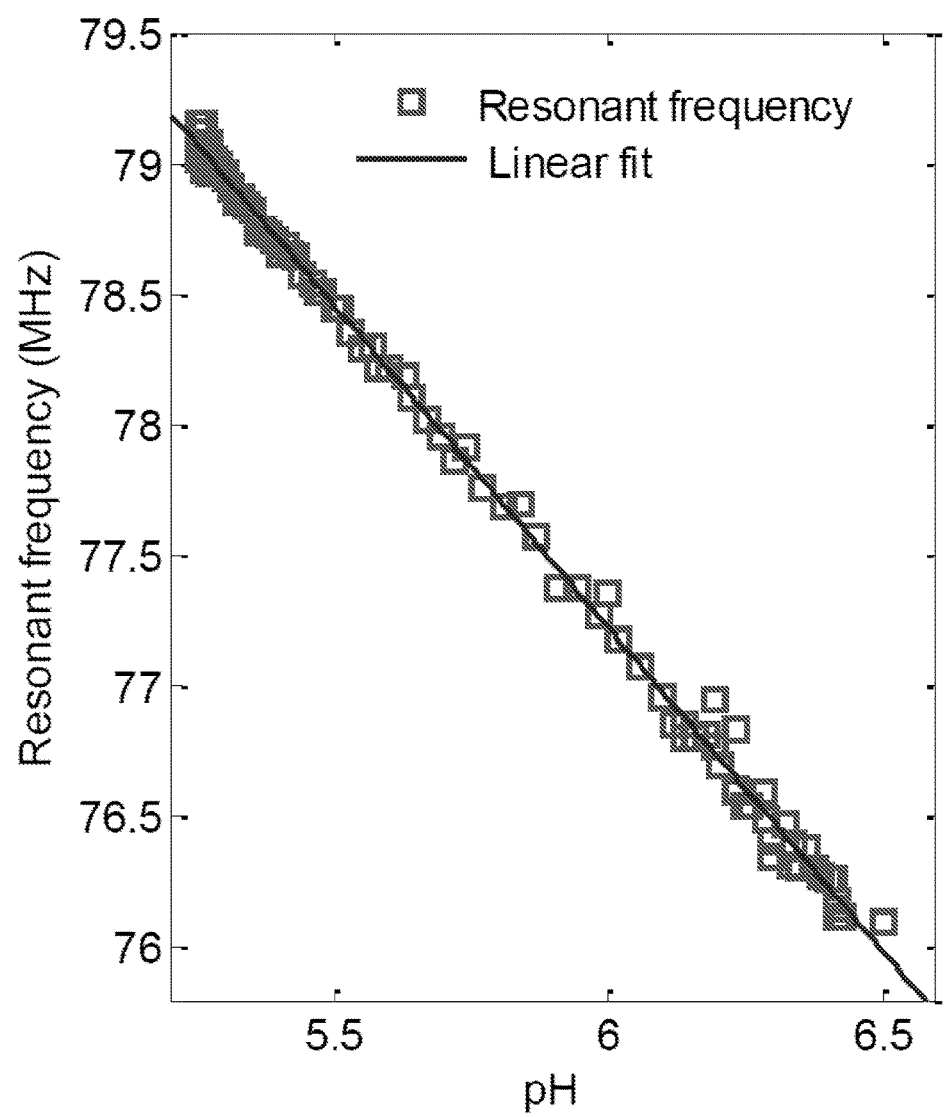
FIG. 27 is a graph of a resonant frequency of an exemplary sensor of the system of FIG. 24 versus the pH of the medium.

FIG. 27 shows the relationship between the pH of the medium (e.g., measured with the commercial pH probe) and the resonant frequency of the sensor 600 excluding the data obtained during first 2.5 hours. A linear fit given by $f_0$ (MHz)=−2.46 pH+91.983 over 6.5-5.26 pH range indicates that the sensor 600 has a 2.46 MHz/pH sensitivity with a maximum deviation of 0.17 MHz (<0.07 pH) from linear fit.

As shown by this example, the exemplary wireless passive pH sensor 600 based on a LC resonator may be capable of real time and repeatable in-fluid pH measurement inside a small bioreactor. The sensor 600 was successfully used in a shake flask set up to provide continuous remote measurement of the pH of Yarrowia iipolytica fermentation, and the pH recorded by the sensor was in good agreement with values measured with a commercial pH probe with a maximum discrepancy of 0.07 pH from a pH of 6.5 to a of 5.26.

Further, the robust and sterilizable sensor 600 was not affected by the electrically lossy medium, and the size of the sensor 600 is suitable for pH monitoring inside a shake flask or test tube.

It will be recognized that various other structures and steps described below may be included and/or may be optional. Further, the description herein includes various features of devices, systems, and methods. One or more of such features may be used separately or in combination according to the present disclosure.

All references cited herein are incorporated in their entirety as if each were incorporated separately. This present disclosure has been described with reference to illustrative embodiments and is not meant to be construed in a limiting sense. Various modifications of the illustrative embodiments, as well as additional embodiments, will be apparent to persons skilled in the art upon reference to this description.

What is claimed:

1. A system for use in wireless transmission of a parameter, wherein the system comprises:
a passive sensor device locatable proximate a material, wherein the passive sensor device comprises a resonant circuit, wherein the resonant circuit comprises:
a sensing portion configured to be used to measure a parameter of the material, wherein at least a portion of the sensing portion is exposable to the material, and
a circuit portion electrically coupled to the sensing portion, wherein the circuit portion is configured to measure the parameter using the sensing portion and to measure a temperature proximate the sensing portion, wherein the circuit portion is further configured to wirelessly transmit a signal representative of the measured parameter and the measured temperature when energized; and
an interrogator portion locatable proximate the passive sensor device, wherein the interrogator portion comprises interrogating circuitry configured to wirelessly transmit energy to the circuit portion of the resonant circuit of the passive sensor device and to wirelessly receive the signal representative of the measured parameter and the measured temperature from the circuit portion of the resonant circuit of the passive sensor device, wherein the interrogating circuitry is further configured to generate a temperature-compensated value of the parameter based on the received signal.

2. The system of claim 1, wherein the sensing portion comprises:
a first electrode exposable to the material, and
a second electrode exposable to the material,
wherein the circuit portion is electrically coupled to the first electrode and the second electrode and configured to measure a potential between the first electrode and the second electrode.

3. The system of claim 2, wherein at least one of the first electrode and the second electrode comprises a nafion layer.

4. The system of claim 1, wherein the circuit portion is further configured such that the quality factor at the resonant frequency of the signal shifts in response to changes in the measured temperature proximate the sensing portion.

5. The system of claim 1, wherein the circuit portion is further configured such that the resonant frequency of the signal shifts in response to changes in the measured parameter.

6. The system of claim 1, wherein the signal representative of the measured parameter and the measured temperature comprises a single signal.

7. The system of claim 1, wherein the temperature-compensated value is pH.

8. The system of claim 1, wherein the interrogator portion is configured to wirelessly transmit energy to the circuit portion using at least one of a swept frequency source and a time-gated swept frequency source.

9. The system of claim 1, wherein the interrogating circuitry is further configured to wirelessly receive the signal representative of the measured parameter and the measured temperature after a selected period of time has elapsed following energization of the circuit portion of the resonant circuit of the passive sensor device by the wirelessly transmitted energy.

10. The system of claim 1, wherein the circuit portion of the resonant circuit is encapsulated by at least one of a low-loss material and a polymer material.

11. The system of claim 1, wherein the system further comprises a container, wherein the passive sensor device is at least partially embedded within the container, where the container at least partially contains the material.

12. The system of claim 1, wherein the material is perishable material, wherein the system further comprises packaging to contain perishable material, wherein at least a portion of the resonant circuit of the passive sensor device is part of the packaging.

13. The system of claim 1, wherein the circuit portion of the resonant circuit of the passive sensor device comprises an inductive loop coupled to a capacitor that changes capacitance based on at least one of the measured parameter and a potential difference between two electrodes exposed to the material.

14. The system of claim 1, wherein the circuit portion of the resonant circuit of the passive sensor device comprises an inductive loop coupled to a thermistor that changes resistance based on the temperature proximate the sensing portion.

15. The system of claim 1, wherein the interrogator portion is configured to determine the measured parameter and the measured temperature from at least one of the frequency response of the signal and the time response of the signal.

* * * * *